(12) United States Patent
Hwang et al.

(10) Patent No.: US 12,186,043 B2
(45) Date of Patent: Jan. 7, 2025

(54) ROBOTIC ENDOSCOPE CONTROLLER WITH DETACHABLE MONITOR

(71) Applicants: CANON U.S.A., INC., Melville, NY (US); The General Hospital Corporation, Boston, MA (US); The Brigham and Women's Hospital Incorporated, Boston, MA (US)

(72) Inventors: Charles George Hwang, Wellesley, MA (US); Yolonda Lorig Colson, Dover, MA (US); Hisashi Tsukada, Brookline, MA (US); Jacob Schieffelin Brauer, Cambridge, MA (US)

(73) Assignees: Canon U.S.A., Inc., Melville, NY (US); The General Hospital Corporation, Boston, MA (US); The Brigham and Women's Hospital Incorporated, Boston, MA (US)

( * ) Notice: Subject to any disclaimer, the term of this patent is extended or adjusted under 35 U.S.C. 154(b) by 835 days.

(21) Appl. No.: 17/316,057

(22) Filed: May 10, 2021

(65) Prior Publication Data
US 2021/0369366 A1    Dec. 2, 2021

Related U.S. Application Data

(60) Provisional application No. 63/032,274, filed on May 29, 2020.

(51) Int. Cl.
*A61B 34/35* (2016.01)
*A61B 1/00* (2006.01)
(Continued)

(52) U.S. Cl.
CPC .......... *A61B 34/35* (2016.02); *A61B 1/00011* (2013.01); *A61B 1/00045* (2013.01);
(Continued)

(58) Field of Classification Search
CPC ......... A61B 34/35; A61B 34/30; A61B 34/74; A61B 2034/742; A61B 2034/301;
(Continued)

(56) References Cited

U.S. PATENT DOCUMENTS

| 2,975,785 A | 3/1961 | Sheldon |
| 3,253,524 A | 5/1966 | Ashizawa et al. |

(Continued)

FOREIGN PATENT DOCUMENTS

WO    2020/092097 A1    5/2020

OTHER PUBLICATIONS

Berthet-Rayne, P., et al., "The i2Snake Robotic Platform for Endoscopic Surgery", Ann Biomed Eng., Jun. 11, 2018, pp. 1663-1675, No. 6, vol. 10.

(Continued)

*Primary Examiner* — Ryan N Henderson
*Assistant Examiner* — Pamela F Wu
(74) *Attorney, Agent, or Firm* — Canon U.S.A., Inc., IP Division

(57) ABSTRACT

A control system controls an endoscope probe in manual mode or robot mode. The system comprises a handle attached to the probe; a portable display controller connectable to the handle; a robotic controller in communication with the handle and/or the portable display controller; and a support platform to which the probe and the portable device controller are attachable according to control mode. In manual mode, the handle is detached from the platform and connected to the portable display controller such that the probe is manually navigated to a first position inside a lumen. In robot mode, the handle is attached to the platform such that the robotic controller cooperates with the handle to robotically navigate the probe to a second position inside the lumen. The portable display controller includes a control (Continued)

section for manipulating the probe and a display section for displaying images of the lumen acquired in both modes.

9 Claims, 10 Drawing Sheets

(51) Int. Cl.
*A61B 34/00* (2016.01)
*A61B 34/30* (2016.01)

(52) U.S. Cl.
CPC ...... *A61B 1/00112* (2013.01); *A61B 1/00149* (2013.01); *A61B 34/74* (2016.02); *A61B 2034/301* (2016.02); *A61B 2034/742* (2016.02); *A61B 2560/0456* (2013.01)

(58) Field of Classification Search
CPC ... A61B 2034/304; A61B 34/32; A61B 34/37; A61B 34/70; A61B 2560/456; A61B 1/00045; A61B 1/00112; A61B 1/00149
USPC .......................................... 600/131, 146–148
See application file for complete search history.

(56) References Cited

U.S. PATENT DOCUMENTS

| | | | |
|---|---|---|---|
| 3,610,231 A | 10/1971 | Takahashi | |
| 3,788,303 A | 1/1974 | Hall | |
| 4,207,873 A | 6/1980 | Kruy | |
| 5,355,871 A | 10/1994 | Hurley et al. | |
| 8,654,184 B2 | 2/2014 | Murayama et al. | |
| 8,682,416 B2 | 3/2014 | Lin et al. | |
| 9,144,370 B2 | 9/2015 | Kato et al. | |
| 9,737,373 B2 | 8/2017 | Schuh | |
| 10,188,471 B2 | 1/2019 | Brisson | |
| 10,261,223 B2 | 4/2019 | Tearney et al. | |
| 10,288,868 B2 | 5/2019 | Tearney et al. | |
| 10,470,831 B2 | 11/2019 | Cohen et al. | |
| 2007/0135803 A1 | 6/2007 | Belson | |
| 2009/0318758 A1 | 12/2009 | Farr et al. | |
| 2010/0041949 A1 | 2/2010 | Tolkowsky | |
| 2012/0078053 A1 | 3/2012 | Phee et al. | |
| 2013/0046137 A1 | 2/2013 | Zhao et al. | |
| 2014/0005677 A1* | 1/2014 | Shelton, IV | A61B 34/30 219/121.72 |
| 2015/0088161 A1 | 3/2015 | Hata et al. | |
| 2018/0185113 A1* | 7/2018 | Gregerson | A61B 34/35 |
| 2018/0192854 A1 | 7/2018 | Hata et al. | |
| 2018/0243900 A1 | 8/2018 | Tanaka et al. | |
| 2018/0311006 A1 | 11/2018 | Kose et al. | |
| 2019/0015978 A1 | 1/2019 | Takagi et al. | |
| 2019/0261830 A1 | 8/2019 | Banik et al. | |
| 2020/0405425 A1* | 12/2020 | Shelton, IV | A61B 34/20 |

OTHER PUBLICATIONS

Rozeboom, E.D., et al., "Feasibility of joystick guided colonoscopy", J Robotic Surg., 2015, pp. 173-178, No. 9.

\* cited by examiner

ROBOTIC ENDOSCOPE CONTROLLER WITH DETACHABLE MONITOR

CROSS-REFERENCE TO RELATED APPLICATIONS

The present application claims priority to U.S. provisional application 63/032,274 filed May 29, 2020. The disclosure of the above-listed provisional application is hereby incorporated by reference in its entirety for all purposes. Priority benefit is claimed under 35 U.S.C. § 119(e).

BACKGROUND INFORMATION

Field of Disclosure

The present disclosure generally relates to medical devices. More particularly the present disclosure exemplifies various embodiments of a handheld portable display controller for a robotic endoscope system. The handheld portable display controller is applicable for controlling articulated steerable medical devices, such as robotic endoscopes or catheters.

Description of Related Art

Endoscopy is a medical procedure that allows remote inspection, manipulation, and/or treatment of internal organs using rigid, semi-rigid, or flexile endoscope devices inserted through natural orifices or small incisions. The complexity of anatomical pathways in a patient, the limited flexibility of existing instruments, and the need to use multiple instruments limit such procedures. Endoscopes are generally composed of a passive proximal section and an active distal section. The proximal passive section can be rigid, semi-rigid, or flexible. The distal active section includes a steerable tip that is remotely actuated by tendons and actuation wheels located on the handle of the device. Endoscopes are typically equipped with a camera, a light source, and one or more channels for suction/irrigation for passing necessary medical tools. Typical endoscopic medical tools have 3 or more degrees of freedom (DOF) which allow for at least insertion, rotation and grasping operations. However, confined workspaces and limited visibility of target organs limit the usability of these systems and require one or more highly skilled endoscopists to perform dexterous tasks. For example, four hands are required to manually control the endoscope and its instruments during a simple procedure. To that end, an endoscopist needs to master a combination of accurate tip angulations, shaft management, and instrument insertion procedures, while communicating with an endoscopist assistant to actuate the instrument and hold the endoscopic shaft in a correct position.

To alleviate the complexity of such procedures, several innovative techniques have been proposed. In particular, numerous robotic endoscope systems have been developed. Some of these robotic endoscope systems operate the endoscope probe in a snake-like manner, by controlling (pushing and pulling) tendon wires. However, significant challenges remain in human-robot interface technology. For example, the "snake" robot endoscope has a portion of the procedure that requires the user to manually insert the catheter to a predetermined position in a patient's anatomy (e.g., to the first carina of the lungs). The endoscope user does this while looking through an endoscopic scope view on a monitor, usually mounted on a support platform or on the wall of the operating room (OR).

The snake robot surgical system consists of several components which continuously interact with the support platform. Since the area immediately surrounding the patient is typically very crowded, the design of the support platform system must be compact, multi-functional, and adjustable to optimize user performance and ensure patient safety. To that end, there are several surgical robots on the market, as well as various robotic systems described in patent and non-patent publications, which propose to hold and position equipment to aid the endoscope user.

The following list of patent and non-patent publications is related to manual and robotic endoscope systems. U.S. Pat. Nos. 2,975,785, 3,253,524, 3,610,231, 3,788,303, 4,207,873, 5,355,871, 9,737,373, 10,470,831, US 20100041949, US 20120078053, US 20190261830, Pierre Berthet-Rayne, et al., "The i2Snake Robotic Platform for Endoscopic Surgery", Ann Biomed Eng. 2018 October; 46(10):1663-1675, 2018; and Esther D. Rozeboom, et al., "Feasibility of joystick guided colonoscopy", J Robotic Surg. 9:173-178, 2015. All of the foregoing patent and non-patent publications are incorporated by reference herein in their entirety.

Nevertheless, there remains a need for endoscope robotic systems with improved human-robot interface that can be used in the limited space around patient's body. In particular, there is need for of a device that enables the endoscopist user to perform manual and robotic operations without leaving the patient's bedside or shifting attention from the patient to communicate with assistant personnel or observe remotely mounted displays.

SUMMARY OF EXEMPLARY EMBODIMENTS

According to at least one embodiment of the present disclosure, there is provided an endoscope control system comprising a portable display and controller which offers the ability to control the robotic system in either manual mode or in robot mode. The system comprises: an endoscope probe having a handle attached at the proximal end of the probe; and a portable display controller attachable to the handle and configured to control movement of the probe in either the manual mode or robot mode. The portable display controller includes a control section configured to control steering of at least a portion of the probe, and a display section configured to display endoscope images acquired by the probe under manual mode and/or robot mode.

According to one embodiment, in the manual mode, the portable display controller (500) is connected to the handle (200), and the connected portable display controller and handle allow a user to manually control a first procedure of advancing the probe along a lumen by steering the distal section of the probe using the control section (502) and displaying an image of the first procedure in the display section (505) of the portable display controller (500). In the robot mode, the robotic controller cooperates with the handle to allow the user to robotically control a second procedure of advancing the probe to a second position in the lumen while the user observes an image of the second procedure in the display section of the portable display controller.

The portable display controller offers an improved human-robot interface for robotic endoscope systems. In one embodiment, there is provided a small user input device with a display screen that is right where all the action is, in the hands of the physician right by the patient's body. The physician does not need to look away from the patient, and can hold the portable display controller where it is most comfortable for her or him. To that end, this user input device can include a screen to display endoscope images, and control buttons to operate the endoscope. In some embodiments, the screen can be auto-rotatable so that the user can hold it with either hand, and the screen can have a touch screen graphical user interface (GUI) to operate the endoscopy. The portable display controller can connect directly to the handle and/or to the robotic arm of the system's support platform. The portable display controller can steer the probe during manual mode and/or robot control mode.

According to one embodiment, the portable display controller includes a handheld monitor and a joystick controller. The handheld monitor and joystick controller can be integrated into a single device, or can be configured to separable from each other. The handheld monitor enables users to view procedural information (e.g., endoscope images and patient information) without looking at a monitor located far away on a support arm or wall. The use of the handheld monitor in handheld position or in close proximity to the user opens up the possibility of a having a touch screen GUI in addition to, or in stead of, the joystick controller. In some embodiments, the handheld monitor includes a handle for improving the user's grip or for quickly hooking the monitor to the system's support arm. In this case, it is advantageous that the monitor is configured with an auto-rotatable screen so that endoscope images can be appropriately oriented in any position of the monitor. The integration of endoscope handle with a portable monitor advantageously frees up at least one of the user's hands to perform other tasks during a procedure. Also, integration of a touch screen in the handheld monitor removes the constraint of requiring separate manual and robotic controllers, and a remote display.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objectives, features and advantages of the present disclosure will become apparent from the following detailed description when taken in conjunction with the accompanying figures showing illustrative embodiments of the present disclosure.

DETAILED DESCRIPTION OF EXEMPLARY EMBODIMENTS

Figure 1A:
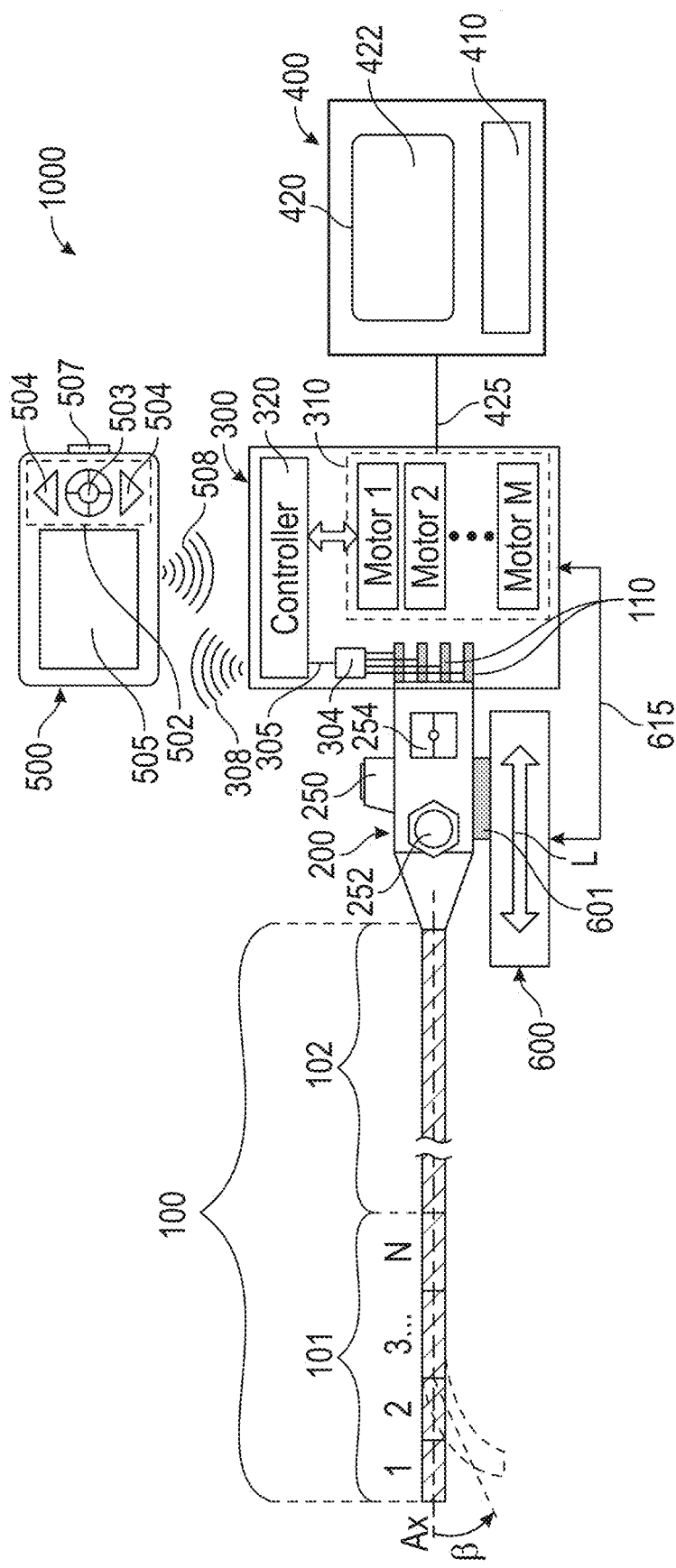
FIG. 1A illustrates an exemplary embodiment of a robotically controlled endoscope probe 100 having a proximal section 102 and a distal section 101; the distal section having multiple steerable segments.

The exemplary embodiments disclosed herein are based on an objective of providing a controller interface applicable to interchangeable manual and robotic control for an articulated steerable medical device having manual insertion mode and robotically controlled navigation mode to guide interventional tools and instruments, such as endoscopes and catheters, through intraluminal tortuous paths.

Throughout the figures, where possible, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope and spirit of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims or some features of a claim may be drafted to exclude any optional element; such claims may use exclusive terminology as "solely," "only" and the like in connection with the recitation of claim elements, or it may use of a "negative" limitation.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to include all sub-ranges subsumed therein. As used herein, the term "substantially" is meant to allow for deviations from the descriptor that do not negatively affect the intended purpose. For example, deviations that are from limitations in measurements, differences within manufacture tolerance, or variations of less than 5% can be considered within the scope of substantially the same. The specified descriptor can be an absolute value (e.g. substantially spherical, substantially perpendicular, substantially concentric, etc.) or a relative term (e.g. substantially similar, substantially the same, etc.).

The present disclosure generally relates to medical devices, and it exemplifies embodiments of a catheter and/or an optical probe which may be applicable to an imaging apparatus (e.g., an endoscope). The imaging apparatus may image using a miniature camera based on chip-on-tip (COT) technology, or may provide some other form of imaging such as spectrally encoded endoscopy (SEE) imaging technology (see, e.g., U.S. Pat. Nos. 10,288,868 and 10,261,223). In some embodiments, the imaging apparatus may include an optical coherence tomographic (OCT) apparatus, a spectroscopy apparatus, or a combination of such apparatuses (e.g., a multi-modality imaging probe).

The embodiments of the optical probe and portions thereof are described in terms of their position/orientation in a three-dimensional space. As used herein, the term "position" refers to the location of an object or a portion of an object in the three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to a total six degrees of freedom); the term "shape" refers to a set of posture, positions, and/or orientations measured along the elongated body of the object. As it is known in the field of medical devices, the terms "proximal" and "distal" are used with reference to the manipulation of an end of an instrument extending from the user to a surgical or diagnostic site. In this regard, the term "proximal" refers to the portion of the instrument closer to the user, and the term "distal" refers to the portion of the instrument further away from the user and closer to a surgical or diagnostic site.

As used herein the term "catheter" generally refers to a flexible and thin tubular instrument made of medical grade material designed to be inserted through a narrow opening into a bodily lumen (e.g., a vessel) to perform a broad range of medical functions. The catheter may be solely an imaging apparatus or it may comprise tools for use in therapeutic or diagnostic procedures. The more specific term "optical catheter" refers to a medical instrument comprising an elongated bundle of one or more flexible light conducting fibers disposed inside a protective sheath made of medical grade material and having an optical imaging function. A particular example of an optical catheter is fiber optic catheter which comprises a sheath, a coil, a protector and an optical probe. In some applications a catheter may include a "guide catheter" which functions similarly to a sheath.

As used herein the term "endoscope" refers to a rigid or flexible medical instrument which uses light guided by an optical probe to look inside a body cavity or organ. A medical procedure, in which an endoscope is inserted through a natural opening, is called an endoscopy. Specialized endoscopes are generally named for how or where the endoscope is intended to be used, such as the bronchoscope (mouth), sigmoidoscope (rectum), cystoscope (bladder), nephroscope (kidney), bronchoscope (bronchi), laryngoscope (larynx), otoscope (ear), arthroscope (joint), laparoscope (abdomen), and gastrointestinal endoscopes.

In the present disclosure, the terms "optical fiber", "fiber optic", or simply "fiber" refers to an elongated, flexible, light conducting conduit capable of conducting light from one end to another end due to the effect known as total internal reflection. The terms "light guiding component" or "waveguide" may also refer to, or may have the functionality of, an optical fiber. The term "fiber" may refer to one or more light conducting fibers. An optical fiber has a generally transparent, homogenous core, through which the light is guided, and the core is surrounded by a homogenous cladding. The refraction index of the core is larger than the refraction index of the cladding. Depending on design choice some fibers can have multiple claddings surrounding the core.

First, structural components of a robotic endoscope system 1000 comprising a robotic endoscope connectable to a handheld portable display controller 500, and attachable to a support platform 600 will be described with reference to FIG. 1A, FIG. 1B, and FIG. 2. The robotic endoscope can be continuum or multi-segment robot configured to form a continuously curved geometry by actuating at least a portion of a steerable endoscopic probe. An example of a continuum robot is a snake-like endoscopic device, as described in applicant's previously published U.S. Pat. No. 9,144,370, and patent application publications US 2015/0088161, US 2018/0243900, US 2018/0311006 and US 2019/0015978, which are incorporated by reference herein for all purposes.

<Configuration of Robotic Endoscope Probe>

FIG. 1A illustrates a general structure of an endoscope probe 100 controlled by a robotic control system 300 which is in data communication with a computer system 400 and/or a handheld portable display controller 500, according to an embodiment of the present disclosure. The endoscope probe 100 has a non-steerable proximal section 102 and a steerable distal section 101 arranged in this order along a longitudinal axis Ax. The steerable distal section 101 includes a plurality of bending segments (1, 2, 3 ... N); and at least one of those bending segments can be actuated to bend the endoscope probe 100 at an angle β with respect to the longitudinal axis Ax. The endoscope probe 100 is controlled by the robotic control system 300 which is mechanically connected to the probe 100 via a handle 200.

The control system 300 generally includes a kinematic controller 320, such as a proportional-integral-derivative (PID) controller or other digital signal processor (DSP) along with suitable software, firmware and peripheral hardware, which are known to persons having ordinary skill in the art. DSPs are generally dedicated integrated circuits; however DSP functionality can also be implemented by using field-programmable gate array chips (FPGAs). The control system 300 can be part of, or is connected to, a computer system 400 (e.g., a system console) which is operated by a processor or central processing unit (CPU) 410. The computer system 400, the robotic control system 300, and the handle 200 are operably connected to each other by a network connection or cable bundle 425. Alternatively or in addition, the control system 300 and/or handle 200 can be connected to the handheld portable display controller 500 via wireless or wired data communication, in a known manner. For example, the control system 300 or the handle 200 may include a wireless transceiver 308 to establish data communication with the portable display controller 500 via a corresponding wireless transceiver 508.

Among other functions, the computer system 400 can provide a surgeon or other user with an image display device 420 and a graphical user interface (GUI) 422 to interact and remotely operate the endoscope probe 100. Similarly, the handheld portable display controller 500 can provide the user with a control section 502 and an image display section 505 to interact and operate the endoscope probe 100. The control section 502 may include manual controls such as a joystick 503 and a plurality of directional keypads 504. The display section 505 may include a display screen for displaying a live image and/or a touch screen with a GUI. As discussed more in detail below, the portable display controller 500 is configured to be connected to the endoscope handle 200 for data communication, by direct attachment, by wire connection, and/or wireless connection therebetween. To that end, the portable display controller 500 may also include a data connection terminal 507 (e.g., RS323 connector, a USB or HDMI port) and/or wireless transceiver 508 (e.g., a WiFi® or Bluetooth®) transceiver.

The robotic control system 300 includes an actuator system 310 in data communication with the controller 320. The actuator system 310 includes a plurality of actuators or actuating motors (Motor 1 through M) equal to a plurality of control wires 110 necessary for actuating and steering the probe 100. The robotic control system 300 also includes and/or controls one or more sensors 304. Sensors 304 can include a strain sensor and/or a position sensor which serve to detect and/or measure compressive or tensile forces applied by the actuators to drive each control wire 110. These sensors 304 also output a signal 305 corresponding to the amount of compressive or tensile force (an amount of strain) being applied to a control wire 110 at any given point in time. The sensors 304 could also output a signal 305 corresponding to an amount of movement (a distance) of displacement for each actuated control wire 110 at any given point in time. The signals 305 from the sensors 304 (strain sensor and/or position sensor) for each control wire 110 are fed into the controller 320 to control each actuator and wire 110 individually with a feedback control loop. In this manner, each control wire 110 can be actively controlled to implement appropriate shaft guidance for navigating the probe 100 through intraluminal paths of a patient's anatomy.

The handle 200 provides electromechanical interface between the endoscope probe 100 and the control system 300. For example, the handle 200 may provide mechanical, electrical, and/or optical connections, and a data/digital acquisition (DAQ) system for interfacing the endoscope probe 100 with the control system 300. The handle 200 may also provide an access port 250 to insert medical tools, one or more mechanical dials or knobs 252 that an operator can use to manually control operations of end effectors and/or steering of the probe 100, and a user interface 254 having one or more control buttons and status indicators. The handle 200 is attachable to a robotic platform 600 which includes a linear stage 601 to move the endoscope probe 100 in a linear direction L. The controller system 300 sends control signals to the platform 600 and linear stage 601 via the handle 200 or an additional connection such as a cable bundle 615.

As part of the user interface 254, the handle 200 may include one or more than one light emitting diode (LED) for providing operational status of the robotic endoscope probe 100 to a user. In an embodiment, the LED may include, for example, different light colors for respectively indicating normal operations (green light) and abnormal operations (red light). Alternatively, the LED may include blinking codes, for example, to indicate a type of abnormal operation. In addition, the user interface 254 may include an emergency on/off switch to manually stop actuation of the endoscope probe 100, in the event of an emergency.

Figure 1B:
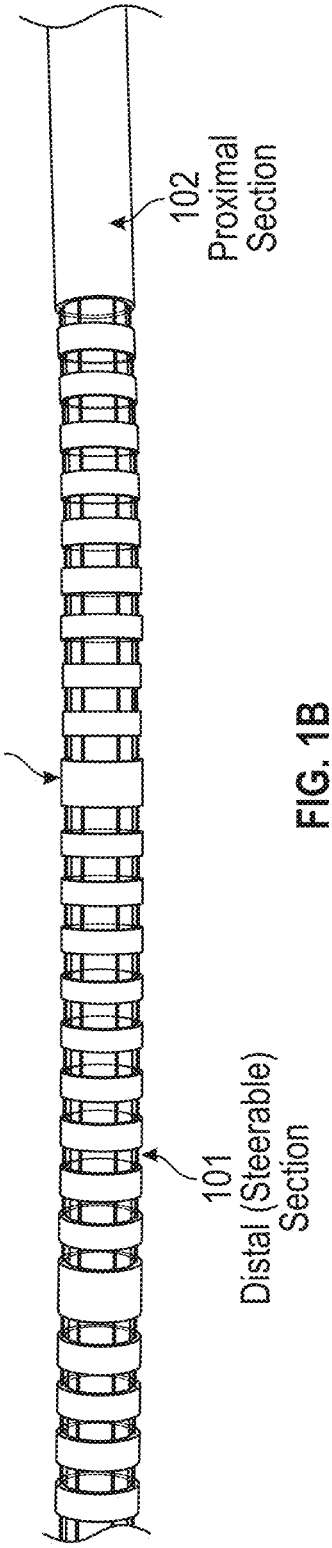
FIG. 1B shows a photograph of an exemplary implementation of the endoscope probe 100.

FIG. 1B shows a perspective view of an exemplary endoscope probe 100. According to one embodiment, the endoscope probe 100 includes a sleeve or sheath made of a tubular non-steerable proximal section 102 and a steerable distal section 101 made of plurality of ring-shaped wire-guiding members arranged at a predetermined distance from each other. The endoscope probe 100 may have an outer diameter of about 0.14 inches, with the distal section 101 being around 2.0 inches in length, and the total length of the probe 100 being about 24 inches. In the distal section 101, control wires 110 are anchored at one or more bending points (inflection points 107) to ring-shaped anchor members. In the proximal section 102, the control wires advance through the proximal end of the probe to the handle 200. The wire-guiding members and anchor members are typically constructed from polyether block amide (e.g., Pebax®). A thin outer sheath and/or inner sheath made of medical grade lubricious material covers the outer and/or inner surface of the tubular shaft. The outer sheath can also be made of Pebax. However, Pebax is only one example, other composites or plastics are viable, e.g., polyurethane.

Figure 2:
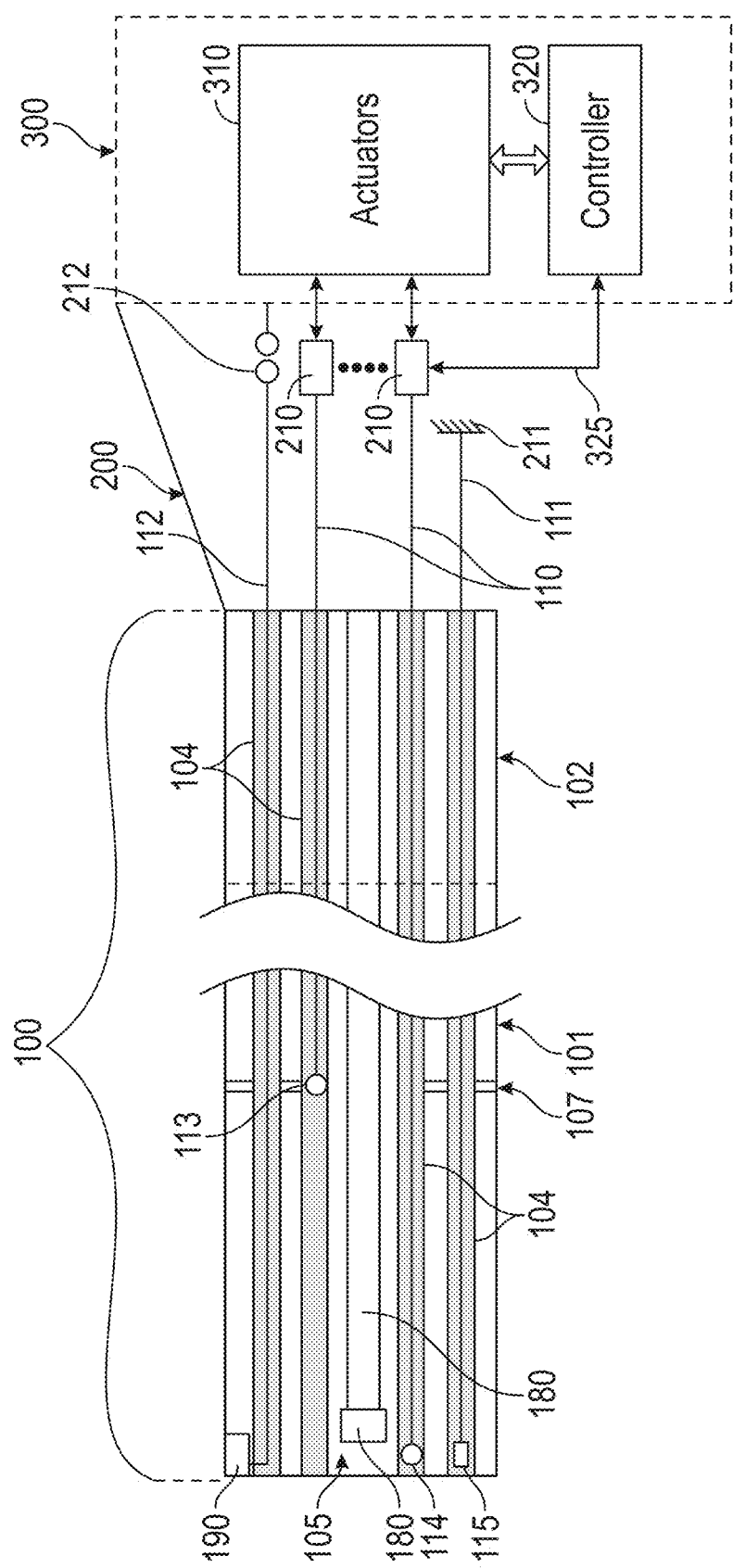
FIG. 2 illustrates in more detail the structure of a steerable endoscope probe 100 which includes a tool channel 105 and a plurality of wire-guiding conduits 104.

FIG. 2 illustrates in more detail the structure of endoscope probe 100 which includes an elongated flexible shaft (elongate body) commonly referred to as a sleeve or sheath (shown in FIG. 1B). This sleeve or sheath has a tubular body having a proximal section and distal section, which includes one or more than one tool channel 105 and a plurality of wire conduits 104 spanning along the length of the sheath from the proximal end to the distal end. The tool channel 105 extends along (typically inside) a cylindrical opening of the tubular body (i.e., in the opening of the sheath), and the plurality of wire conduits 104 extend along (typically within) the wall of the sheath. As it can be appreciated by persons skilled in the art, tool channel 105 and wire conduits 104 are not limited to any specific cross-sectional shape; the cross-section of the tool channel and wire conduits can be circular, substantially circular, or polygonal as long as the functionality of the endoscope probe is not negatively affected.

The tool channel 105 includes an imaging device 180, but it also allows passage for end effectors to be delivered and operated at the distal end of the sheath. For this reason, the imaging device 180 can be removably arranged in the tool channel 105, so that the imaging device 180 can be repositioned within the tool channel and/or swapped for other components like end effector tools used during a procedure. In addition, tool channel 105 may also be used for delivering and/or retrieving fluids, such as liquid or gaseous substances (e.g., air, water) to/from a target area within a bodily lumen. The imaging device 180 may include an endoscope camera, or a fiber-based imaging probe. An example of an endoscope camera includes, but is not limited to, a chip-on-tip (COT) camera, such as a camera with a miniature CMOS sensor arranged at the tip of the imaging device. Examples of fiber-based imaging probes include, but are not limited to, a near infrared auto-fluorescence (NIRAF) imaging probe, a spectrally encoded endoscopy (SEE) probe, an optical coherence tomography (OCT) imaging probe, an intravascular ultrasound (IVUS) probe, or combinations thereof.

The wire conduits 104 allow anchorage and/or passage of control and support wires used for steering (bending, twisting or rotating) the steerable distal section 101 of the sheath. Some wire conduits 104 may be used for passing optical fibers and/or electrical cables. The bending segments (1, 2, 3 . . . N shown in FIG. 1A) are joined to each other at one or more than one inflection point 107. At the proximal end of the sheath, the handle 200 provides a physical interface between endoscope probe 100 and the control system 300.

The endoscope probe 100 is configured to provide flexible access for an array of instruments allowing remote imaging, manipulation, cutting, suturing, delivery and retrieval of fluids, etc., to intraluminal target areas inside a patient's anatomy. To that end, the endoscope probe 100 must provide flexibility for navigating through tortuous paths, while retaining torsional and longitudinal rigidity so that the user can control the instruments located at the distal end of the sheath, by remotely operating such instruments with the control system 300. To provide steerable functionality, the endoscope probe 100 is equipped with one or more support wires 111 and a plurality of control wires 110, which are arranged inside the wire conduits 104 along (typically inside) the wall of the sheath. Some of the control wires 110 are anchored at the distal end of the sheath (in the distal section 101) using wire anchors 114. Other control wires 110 can be anchored at certain distances from the distal end (e.g., at an inflection point 107) using wire anchors 113.

In one exemplary embodiment, an endoscope probe 100 can be steered by six wires including one pair of support wires 111 and two pairs of control wires 110. A first pair of control wires 110 can be anchored by wire anchors 113 at inflection point 107 of the steerable distal section 101 of the sheath. A second pair of control wires 110 may be anchored by wire anchors 114 at the distal end of the steerable distal section 101. Support wires 111 are anchored to a fixed (stationary) structure 211 at the proximal end and to support anchors 115 at the distal end (or at an inflection point) of the steerable section 101. The support wires 111 act as "tendon" wires to restore (counter) a steering action exerted by the control wires 110. In some embodiments, the support wires 111 can be actively controlled in the same manner as the control wires 110. In this manner, the endoscope probe 100 can have the steerable section 101 with at least two (i.e., two or more) bending sections each controlled by pairs of antagonistic wires running through wire conduits 104. It is understood that each bending section can be controlled by more than two antagonistic wires.

While the case of driving control wires 110 for steering one or two segments of the steerable section 101 has been described above, if control wires 110 of all bending segments are driven, the postures of each bending segment may be independently controlled in accordance with the driving amounts of the individual control wires 110. Further, a mechanism that twists or rotates the wire-driven endoscope probe 100 around the longitudinal axis may be provided. In the case of providing rotation or twisting action to the endoscope probe 100, a first segment may be bent in a desirable direction by driving only one control wire 110 and then rotating the entire sheath about its longitudinal axis can control torsional movement of the distal tip of the sheath. Additional details for driving the snake robot include the control methods for actuation, as described in applicant's previous patent application publications US 2015/0088161, US 2018/0243900, US 2018/0311006, and US 2019/0015978, which are incorporated by reference herein for all purposes.

At the proximal end of the endoscope probe 100, the handle 200 is configured to provide a mechanical linkage and an electromechanical interface between the endoscope probe 100 and the control system 300. In one embodiment, the handle 200 provides a plurality of electromechanical connections 210 (one connection for each of the control wires 110) so that the actuator system 310 can mechanically operate each control wire 110 individually. In addition, the handle 200 may provide an anchoring or fixing structure 211 (a mechanical ground) for the support wires 111.

In some embodiments, electrical cables 112 are also passed through wire conduits 104. The electrical cables 112 can be connected, on one end (at the proximal end) to a power source terminal 212 provided at the handle 200, and on the other end (at the distal end) to an electronic component, such as tracking sensor, for example, an electromagnetic (EM) sensor 190 located in (typically inside) the wall of the sheath. For example, some endoscope probes may use the EM sensor 190 located at the tip of the instrument to obtain an electromagnetic signal (EM data) for sensing the position and/or orientation of the instrument's tip and controlling registration and navigation of the instrument, based on such EM data.

More specifically, as mentioned above, the electronic controller 320 is used to drive the actuators (motors) of the actuator system 310 to electronically control the operation of each control wire 110 by applying tension, torsional, or compressive forces to each control wire 110. The controller 320 can control each control wire 110 by actively driving by an actuator or motor (310), a sensor (304 or 190), and a feedback control loop 325 to implement appropriate shaft guidance for navigating through tortuous intraluminal paths of a patient's anatomy. A typical 6DOF EM sensor with a sub-millimeter diameter and about 5 mm length can measure both position and orientation of the object to which such sensor is attached. Therefore, the EM sensor 190 can be used to measure the bending, twist, or rotation of the distal section 101. In addition, the EM sensor 190 can track the position and/or orientation of imaging device 180 to maintain image orientation in the display section of the portable display controller 500. Therefore, the signals 305 can include not only strain and displacement signals, but also position and/or orientation of the distal end of the steerable distal section to accurately track any twist, bend, or rotation of the probe.

In addition, either during insertion or retraction of the endoscope probe, the control system 300 controls the linear stage 601 of support platform 600 to move the probe 100 along the center line of the lumen (e.g., an airway) in a desired trajectory followed by active control of the bending sections. This is similar to known shaft guidance techniques used to control robotic guided catheters or endoscopes with the goal of forcing the flexible shaft to keep to the desired trajectory. In one example, when using a shaft guidance system, the endoscope probe is robotically advanced through a lumen while sensors measure the insertion depth of the shaft-guide and the angulations of user-controlled steerable tip segments to obtain trajectory information. The trajectory information is stored in a memory of the system and continuously updated. After a short advance in insertion or retraction distance, the shape of the steerable shaft-guide is corrected by adjusting (rotating or bending) segments of the instrument in such a way that the new shape closely matches the desired trajectory. This process is repeated until a target area is reached. A similar process can be applied when the endoscope probe is withdrawn from the patient. See, e.g., US 2007/0135803, which is incorporated by reference herein for all purposes.

However, before performing robotic controlled navigation along the length of the lumen, it is desirable to manually insert the probe 100 to a predetermined location (a first location) along the longitudinal direction of the lumen. For example, in robot-assisted bronchoscopy, it is advantageous to manually insert a steerable catheter to the first carina of the patient lungs, and then perform robot-assisted navigation thereafter (in the manner described above). Since, the probe can contact the patient's anatomy and this can cause discomfort and/or pain to the patient, the present disclosure provides a novel control mechanism with integrated display and control functionality that can be seamlessly operated in manual mode or robot mode.

Manual vs. Robot Mode—The Snake robot system includes a console with support platform (arm) and removable tethered handle. Disposable catheter is connected to handle and inserted into the patient, steered with manual mode to first carina. Manual mode has only simple functions like up/down/left/right that exist on current endoscopes. Once the catheter is at the first carina, the user attaches the handle to the support platform (arm), and the mode switches to robot mode. Once the system is in robot mode, the system controller operates the linear stage of the support platform, and the user can steer the probe in sophisticated robotically-enabled ways like the follow-the-leader or "chicken head" techniques. See, for example, U.S. Pat. Pub. 2018/0192854 and WO/2020/092097. These advanced movements are not possible without robotic control, but are enabled by portable display controller disclosed herein.

<Controller with Detachable Portable Monitor>

Figure 3B:
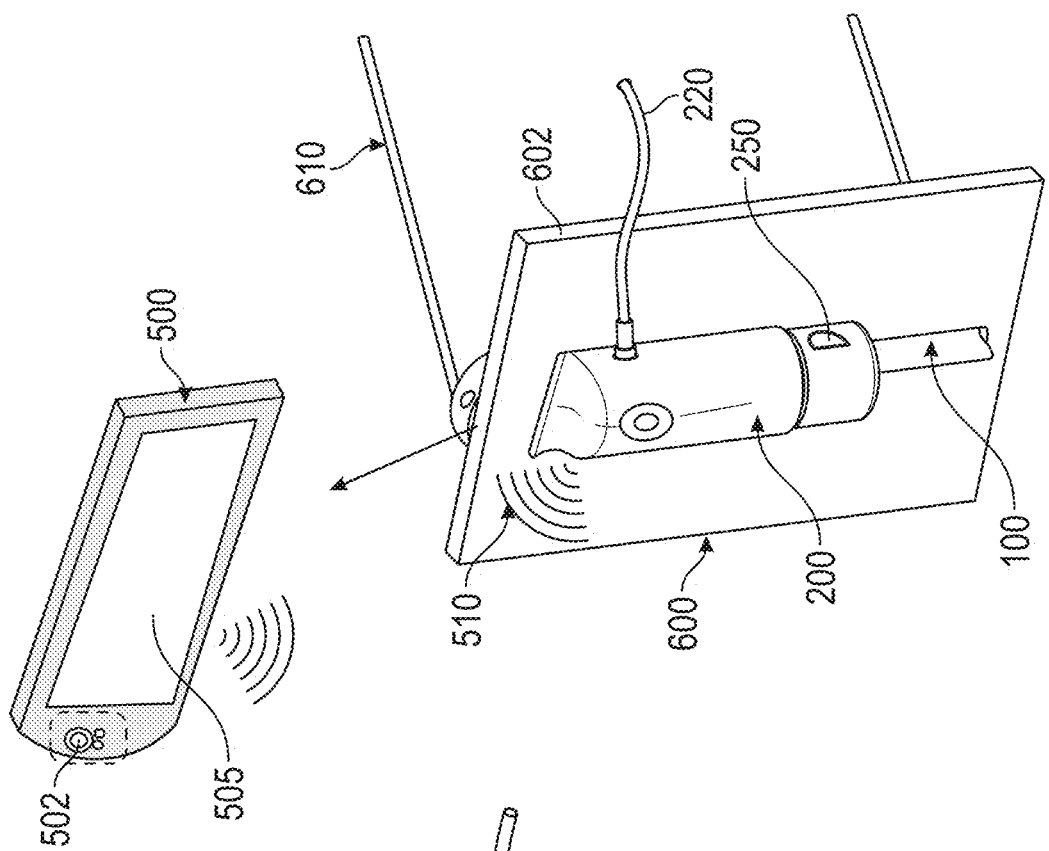
FIG. 3B shows an embodiment of the handheld portable display controller 500 configured to connect to the endoscope handle 200 via wireless communication.
Figure 3A:
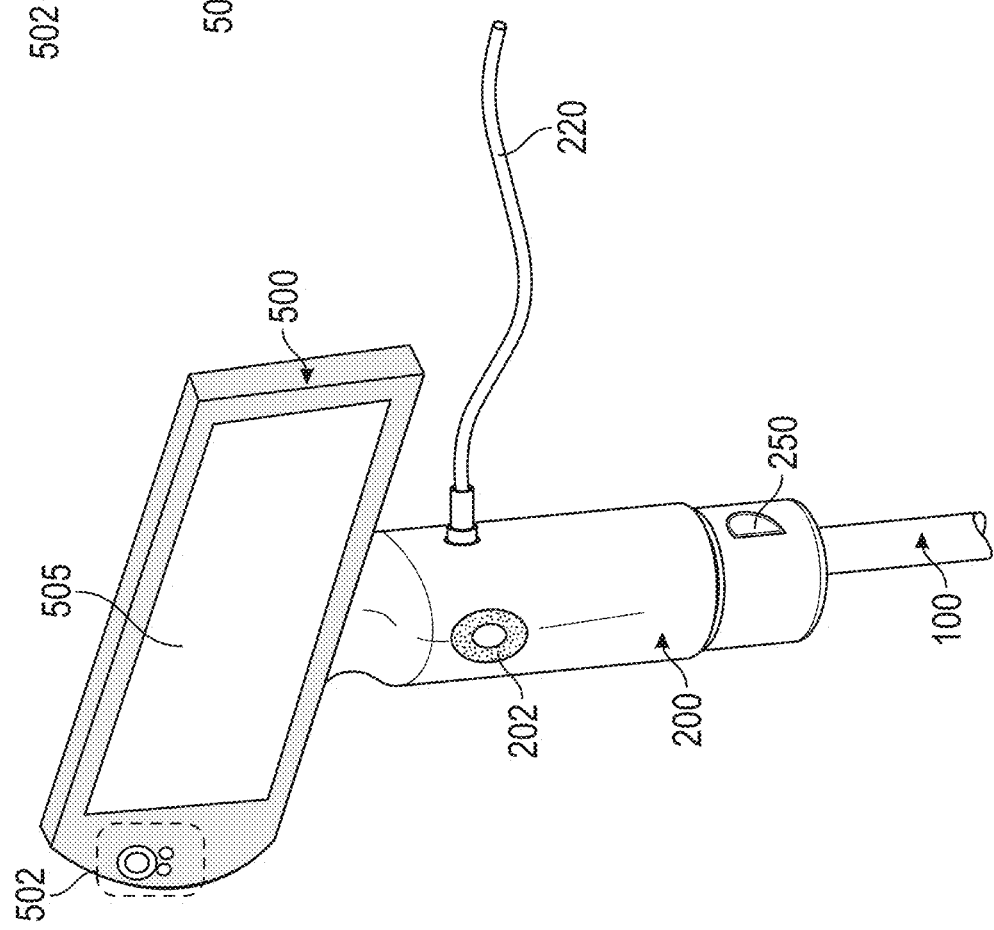
FIG. 3A shows an embodiment of a handheld portable display controller 500 combined with an endoscope handle 200 and configured to control an endoscopic probe 100, according to the present disclosure.

FIG. 3A shows an embodiment of an endoscope controller interface which is implemented by a handheld portable display controller 500 configured to be connected or attached to the endoscope probe 100 according a manual mode or robot mode of an endoscope procedure. The controller interface includes a detachable handheld portable display controller 500 which is connectable to an endoscope handle 200, which in turn is connectable to a steerable endoscope probe 100. FIG. 3B shows the endoscope handle 200 mounted onto a robot support platform 600 and wirelessly connected to the handheld portable display controller 500. In manual mode, the user physically holds the display controller and the handle to manually insert and/or retract the probe into an anatomy of the patient while controlling the tip of the probe with the user interface (control section 502). In robot mode, the motion of insertion or retraction of the probe is completely actuated by robotic control system 300 which controls the operation of the linear stage 601 and one or more links of the support platform 600.

The handheld portable display controller 500 is a portable monitor which includes as least a control section 502 and a display section 505. The portable display controller 500 generally includes, as part of the display section 505, a display screen (e.g. an LCD or OLED display), a housing, illumination and imaging control electronics, image processing electronics, a power supply cable and/or a rechargeable battery. The endoscope handle 200 includes a connection indicator 202, an access port 250, and a cable bundle 220. The connection indicator 202 is configured to inform the user that the handheld portable display controller 500 is operatively connected to the handle 200. The connection indicator 202 may include, for example, a light emitted diode (LED), haptic feedback unit (vibrating surface), a sound emitting unit (speaker or buzzer), other similar device capable of informing the user of a connection status between the handle 200 and the handheld portable display controller 500. The access port 250 is used to insert endoscopic tools into the tool channel 105 of the probe 100. The cable bundle 220 includes at least a power cable and a video cable, and it serves to establish data communication between the endoscope handle 200 and computer system 400.

As shown in FIG. 3A, the handheld portable display controller 500 can be removably attached (physically connected) to the proximal end of handle 200. However, as further describe below, the handheld portable display controller 500 can also be connected to the endoscope handle 200 by a wireless or wired network. When the handheld portable display controller 500 is connected to the handle 200, at least part of the control section 502 is directly accessible to the user for manual operation while, at the same time, the user can observe an endoscope image on a screen of the display section 505. For example, certain controls, such as a joystick, a multi-directional touchpad or keypad, or a touch screen GUI can be accessible to the user.

The intent of this configuration is for manual insertion of the endoscope probe into a patient's anatomy prior to robotic control, so a simple joystick or directional keypad would suffice the required functionality to control the tip of the probe (catheter or endoscope). Other controls, such as buttons for activating irrigation or suction, can be disabled, eliminating the possibility of inadvertent activation and/or confusion by the user. Accordingly, the user can freely control the manual insertion of the probe 100 into a luminal anatomy of the patient without worrying about accidentally touching other buttons of control section 502. Here, during manual operation, the probe movement in or out of the patient's anatomy can be user controlled, by manually pushing or pulling the handle 200 toward or away from the patient, while observing an endoscope image acquired by the probe and displayed on the handheld portable display controller 500.

FIG. 3B shows the handheld portable display controller 500 mounted onto a robot support platform 600. In this configuration, the handheld portable display controller 500 is connected to the handle 200 via a wireless connection 510, but it is not physically attached to the proximal end of the handle 200. In this configuration, while the endoscope handle 200 is mounted onto the support platform, the user can grab the handheld portable display controller 500 and have access to the control section 502 (e.g., joystick), for example, by using its thumb, while observing a live image in the display section 505.

Figure 3C:
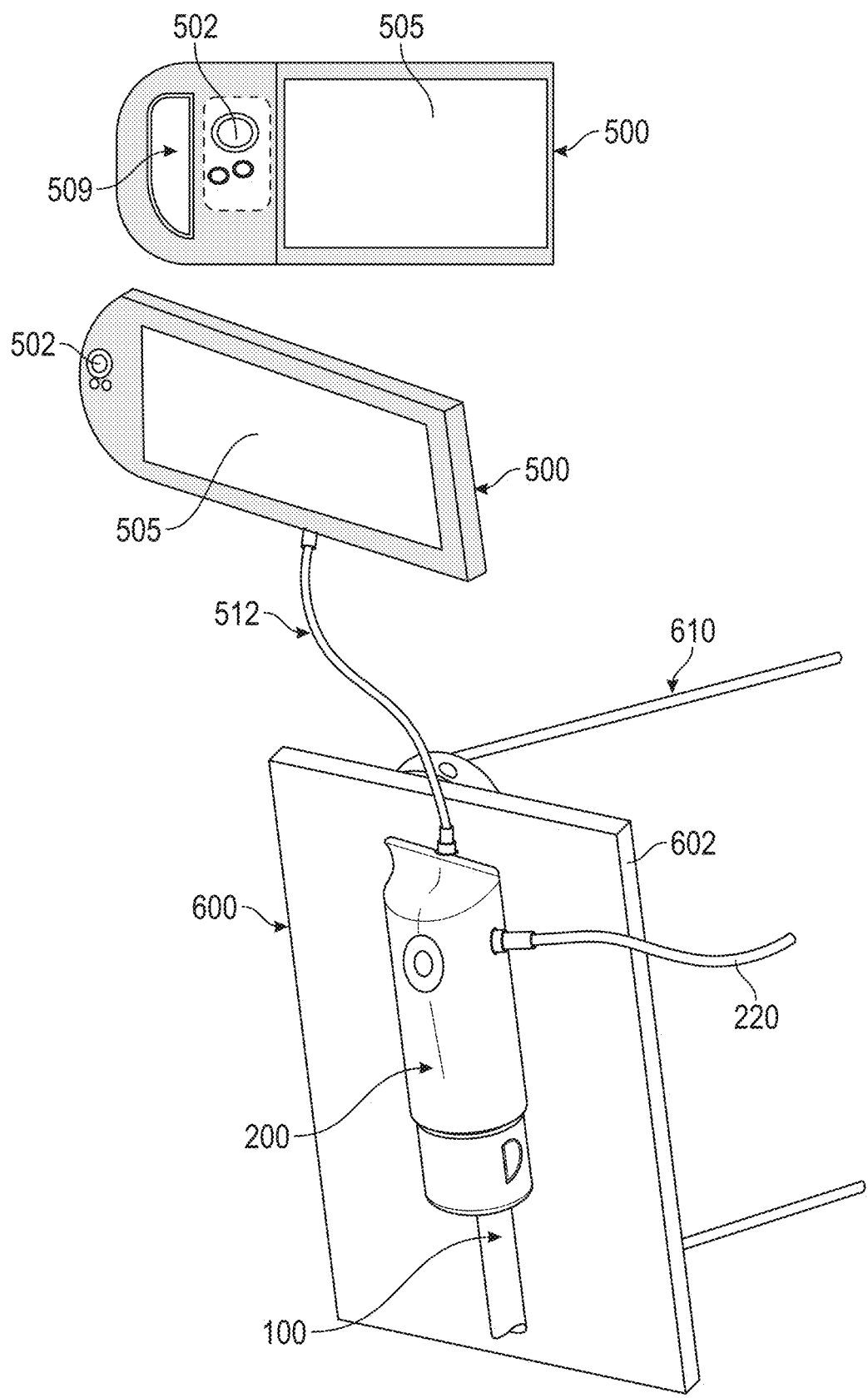
FIG. 3C shows an embodiment of the handheld portable display controller 500 configured to connect to the endoscope handle 200 via wired communication.

FIG. 3C illustrates a configuration where the endoscope handle 200 is mounted onto the robot support platform 600 and connected to the portable display controller 500 via wired connection 512. In this manner, the handle 200 can establish data communication with both the portable display controller 500 (via the wired connection 512) and with the main control system 300 (via the cable bundle 220). The wired connection 512 may include any suitable video data interface (e.g., an HDMI interface) and/or a separate data connection (e.g., a USB connection). The structure of the support platform 600 is the same in FIG. 3A and FIG. 3B. In this embodiment, the cord of the wired connection 512 may be detachable from both ends, or it may be retractable on at least one end. In this manner, when the portable display controller 500 is not in use, the cord of connection 512 can be retracted into the handle 200, into the controller 500, or completely removed. In robot mode, the handle 200 is attached to the support platform 600, and the corded portable display controller 500 is detached from the handle 200 and used for observing live images of the ongoing procedure. In some embodiments, the portable display controller 500 can be provided with a handle 509 to allow a secure grip by a user's hand. In this case, the control section 502 is strategically located adjacent to the handle 509 so that the user can control the joystick and/or buttons with a single thumb action. Moreover, the portable display controller 500 with a handle 509 can be configured with an auto-rotatable screen so that the user can use the controller 500 with either hand (i.e., with left-handed or right-handed control).

Once the endoscope handle 200 is docked on the support platform 600, the control system 300 enters the robotic control mode. Specifically, as shown in FIG. 3C, the portable display controller 500 is removed from the endoscope handle 200, and the endoscope handle 200 can then be connected to the robotic control system 300 via the console cable bundle 220. To facilitate safe removal of the portable display controller 500, the endoscope handle 200 can be configured to inform the user of the attachment status thereof by activating or deactivating the connection indicator 202 when the manual operation is completed and the handle 200 is placed on the support platform 600. In this manner, the user can be made aware that the portable display controller 500 is available for removal from the handle 200.

Figure 4A:
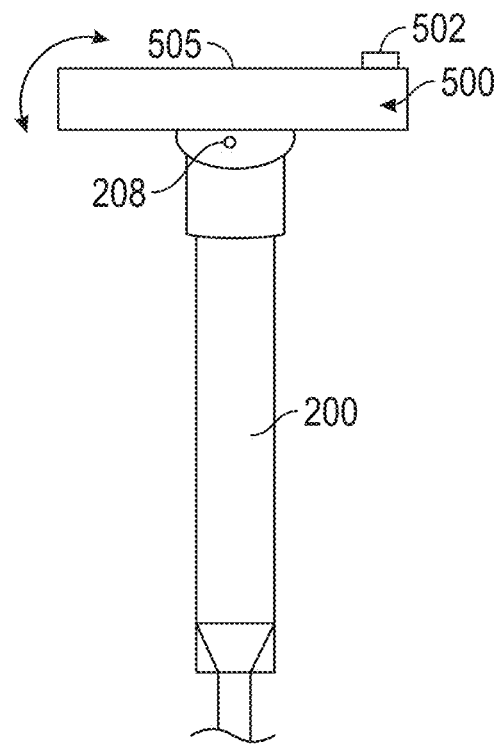
FIG. 4A and FIG. 4B show a side and perspective view of an embodiment of a tiltable handheld portable display controller 500 configured to connect to an endoscope handle 200.
Figure 4B:
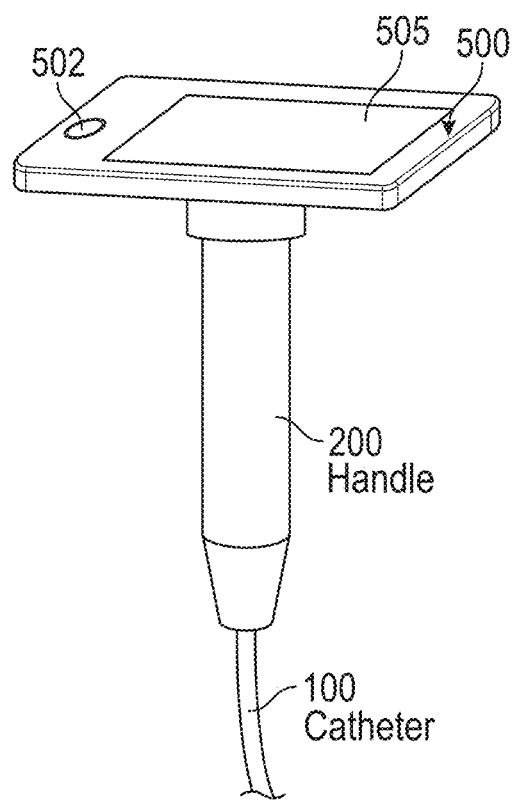

FIG. 4A and FIG. 4B illustrate another embodiment of the portable display controller 500 removably connected to the endoscope handle 200. The concept described in this embodiment is the portable display controller 500 implemented as a removable, tiltable handheld monitor with a simple joystick control for maneuvering the catheter tip during manual insertion. In this embodiment, the endoscope handle 200 is provided with a proximal connecting portion 208 which is configured to interface with a similar connection in the portable display controller 500. The connection portion 208 can be, for example, a RS232 or similar type connector.

In the embodiment shown in FIG. 4A and FIG. 4B, the user first grips the handle 200 to control the probe (catheter insertion/retraction) movement. At the same time, while the user is inserting (or retracting) the probe 100, the user is monitoring the camera view on the monitor (display section 505), while manually steering the tip of the probe 100 using the joystick 503 and/or directional keypads 504 of the control section 502.

Once a predetermined location within the patient's anatomy is reached (e.g., once the first carina of the lungs is reached), the portable display controller 500 is removed (detached) from the handle 200, and the handle 200 is attached to the support platform 600 to initiate navigation and steering under robot mode. In the robot mode, the user now uses the portable display controller 500 (portable monitor) and the control section 502 (joystick and/or keypads) to control the snake-like movement (navigation) of the robotic probe for the remainder of the procedure.

Some of the main elements in the foregoing embodiments of a robotic endoscope system 1000 include an endoscope handle 200 combined with a tilting, detachable handheld monitor (portable display controller 500) to perform a manual control mode for part of an endoscopic procedure. The handheld monitor may included a liquid crystal display (LCD) or an organic light emitting diode (OLED) display device of reduced size and weight substantially similar to a "smart phone" or a portable "video game console"; this handheld monitor may or may not have touch screen capability. The handheld monitor may have a joystick and/or a directional keypad to control the catheter tip during manual insertion mode. The joystick and/or directional keypad (e.g., a touchpad) is a control section which may be incorporated in the handheld monitor, or it can be provided as a separate device to be removably integrated with the handheld monitor.

Once the handheld monitor is detached, the handle 200 is attached to a support platform that is possibly connected to the patient bed, the system cart (console), or other secure site. In any configuration, attaching the handle 200 to the support platform initiates robot mode. When in robot mode, the insertion/retraction of the probe is accomplished by the support platform mechanically moving the handle 200 and the probe in a linear direction (e.g., up/down or forward/backward along the length of the support platform). This movement might be accomplished through known electromechanical controls using typical metal toothed gears, drive belts, magnets, telescopic links, or combinations thereof. Robotic controls of this nature are known to persons skilled in the art from, for example, U.S. Pat. Nos. 10,188,471 or 8,682,416, which are incorporated by reference.

<Robot Support Platform for Handheld Portable Display Controller>

Figure 5:
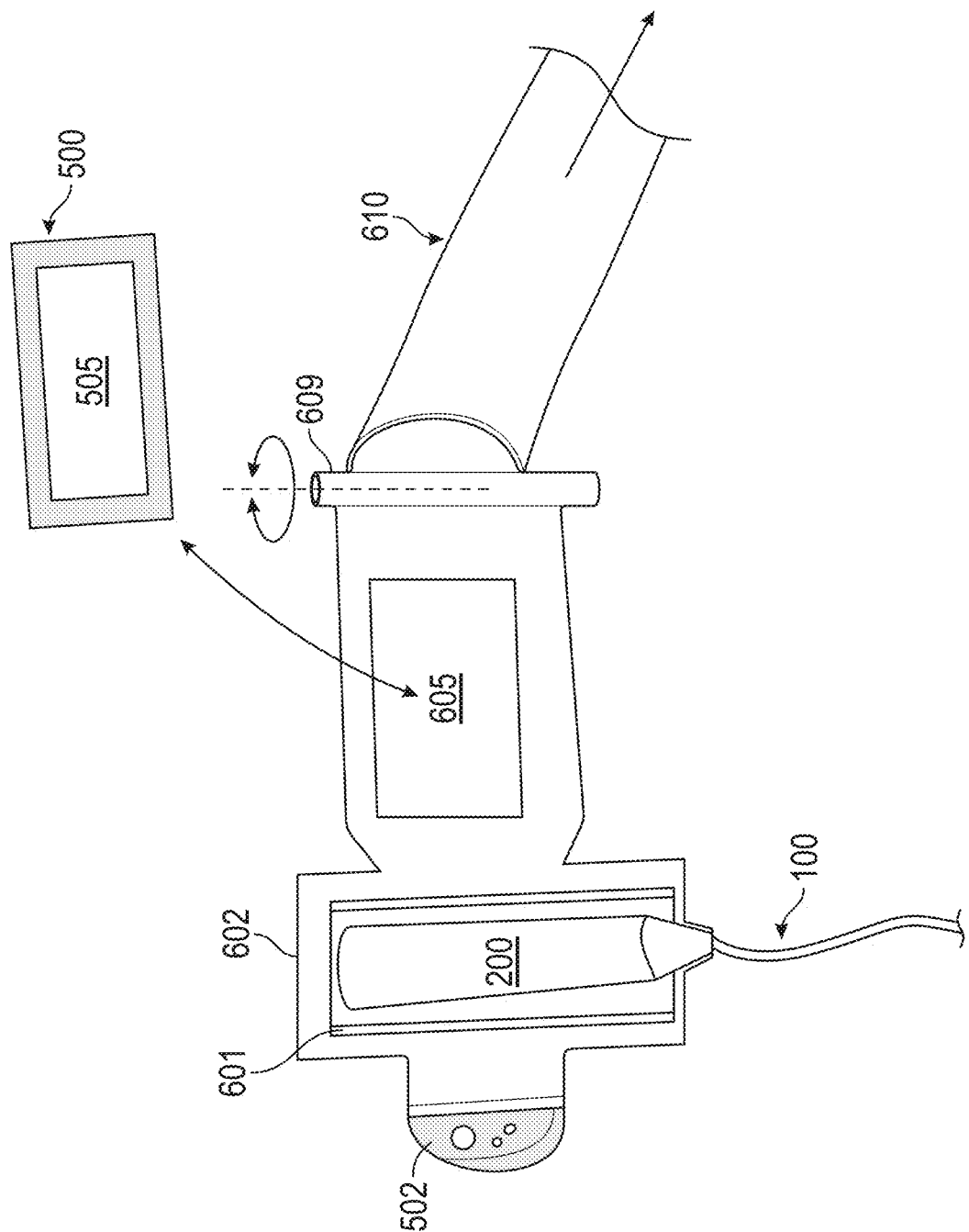
FIG. 5 illustrates an embodiment of a support platform 600 configured to hold the handheld portable display controller 500 for controlling a robotic endoscope probe 100.
Figure 6:
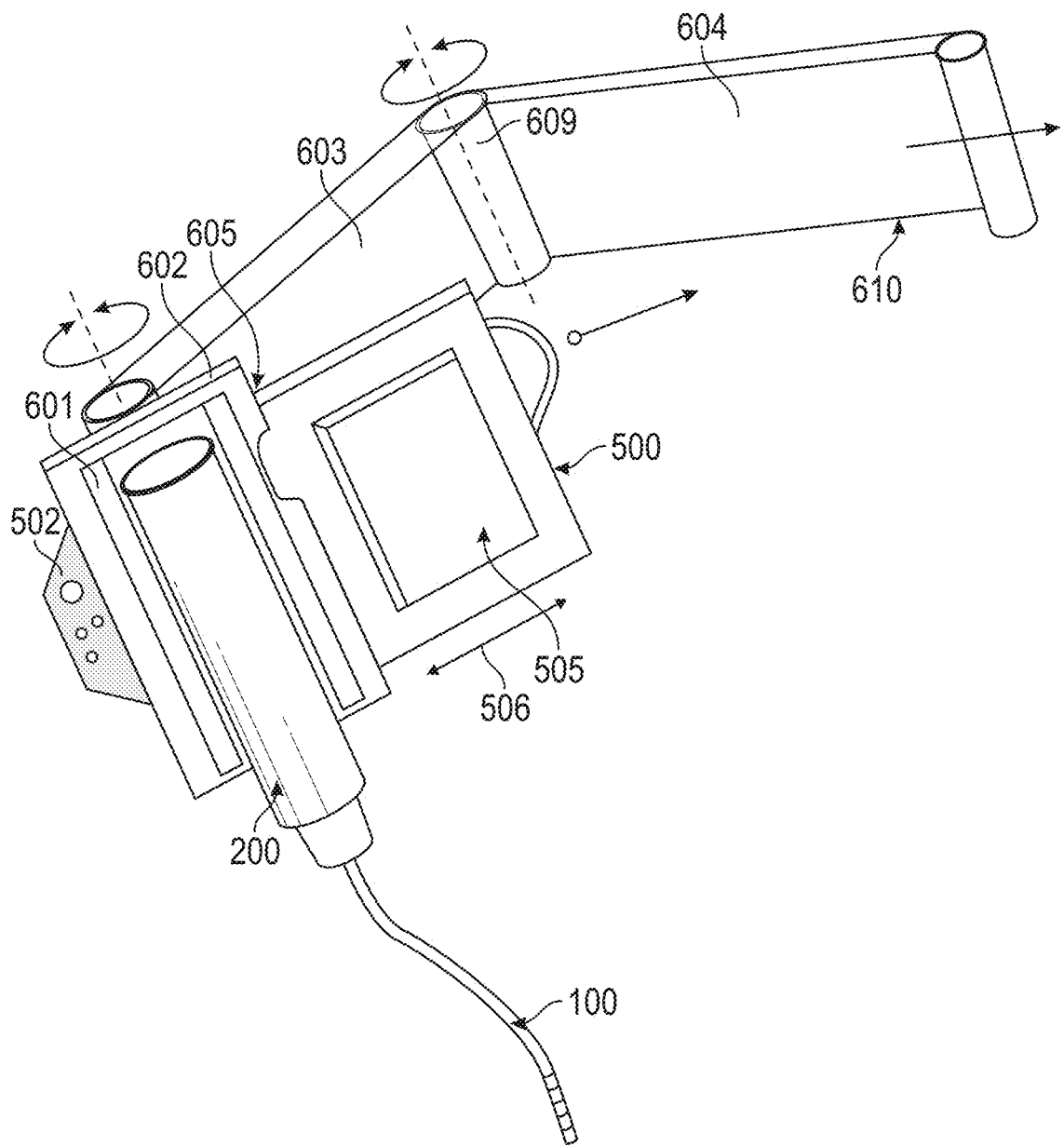
FIG. 6 illustrates an embodiment of a support platform 600 configured to hold the handheld portable display controller 500 for controlling a robotic endoscope probe 100.

FIG. 5, FIG. 6, and FIG. 7 disclose further details of the support platform 600 and the portable display controller 500 which are part of the robotic endoscope system moo. The support platform 600 includes a support plate 602, a linear stage 601, and one or more than one robotic arms. The support platform 600 is configured to attach the snake robot system 1000 to a patient bed or to a console cart unit. The support plate 602, which is a place for the user to attach the handle 200, may also be configured to store, and/or recharge the portable display controller 500 (a handheld monitor). In these exemplary drawings, the portable display controller 500 includes the display section 505 and the control section 502 separable from each other. In these examples, the display controller 500 includes various components similar to those of, for example, the Nintendo Switch console, available from Nintendo Co., Ltd. (Kyoto, Japan).

In FIG. 5, the support platform 600 includes a robotic arm 610, a support plate 602, a linear stage 601, a monitor receptacle 605, and one or more joints 609. The robotic arm 610 may comprise a multi joint arm that includes a plurality of linkages connected by joints 609 (having non-illustrated actuators and encoders) to enable the linkages to rotate, bend and/or translate relative to one another in response to controlling signals from the robot control system 300. The robotic arm 610 may be fixed to a support structure (patient bed or system console) at one end and may have an end effector linkage at the other end with various degrees of freedom.

The support plate 602 is an attachment feature for holding the handle 200 of the endoscope probe 100. The linear stage 601 is a controllable feature configured to physically engage with handle 200 and actuate linear movement the probe 100 in small increments of movement. The monitor receptacle 605 is a place for the user to attach, stow, view, and/or recharge the portable display controller 500. In operation, under the manual mode, the handle 200 is removed from the support plate 602 and connected to the portable display controller 500; the user manually inserts the probe 100 into a lumen while observing live view images in the display section 505 and steering the probe tip with the control section 502 of the controller 500. Upon reaching a predetermined length of insertion, or reaching a predetermined anatomy, the user disconnects the portable display controller 500, and returns the handle 200 to the support plate 602. Once the endoscope handle 200 is attached to the support platform, the system enters a robotically controlled mode. Under the robotically controlled mode, control system 300 controls the support platform to insert and/or retract the endoscope probe 100 into the patient by linear movement of the handle 200 along the linear stage 601.

Optionally, the user, via the control section 502 and the display section 505 of the portable display controller 500, can control and/or observe the actions of the tip of the endoscope probe 100. Specifically, the portable display controller 500 can be used as a remote control for controlling the bending of the endoscope probe tip and possibly other functional controls such as irrigation/suction or image capture. The portable display controller 500 can be a wireless controller which can be docked onto the monitor receptacle 605 of the platform support 600. Providing the monitor receptacle 605 in the robotic arm 610, for example, serves at least three functions, including: (1) provides a place to store the portable display device, (2) provides a place to recharge the wireless portable display device or provides a place to stow the wired portable display device when not in use, and (3) provides a place for the user to temporarily park the portable display device during parts of a workflow procedure that requires the user to have both hands free.

FIG. 6 illustrates a further alternate embodiment of the support platform 600 having a hidden monitor receptacle 605. In this embodiment shown in FIG. 6, the portable display controller 500 can remain hidden behind the support plate 602 when not in use, and is moved in the directions of arrow 506 when in use. In this case, the user can pull the portable display controller 500 out from the monitor receptacle 605 for viewing live images of a procedure. In addition, the user also has the option to completely detach the portable display controller 500 from the support platform 600 for handheld (manual) control and image viewing. Once a procedure is completed, the user replaces the monitor back in the monitor receptacle 605 behind the support plate 602. This configuration allows for a compact, yet versatile environment where the user can advantageously use the portable display controller 500 for manual controlled insertion and robotic controlled navigation while continuously observing the procedure. When the portable display controller 500 is not in use, it is returned to the monitor receptacle 605, which can serve as a display charging station. In addition, while the display controller 500 is in the monitor receptacle 605, the display is protected from damage during transport and/or movement in crowded spaces such as a procedure room. Making the portable display controller 500 removable and storing it in a hidden monitor receptacle 605 is important given how frail display screens are, and given that a procedure room likely contains video monitor equipment, workstations, fluoroscopy equipment, Pyxis medication dispensing stations, a patient bed, an anesthesia cart, and various storage cabinets.

<Console and Control System with Handheld Portable Display Controller>

Figure 7A:
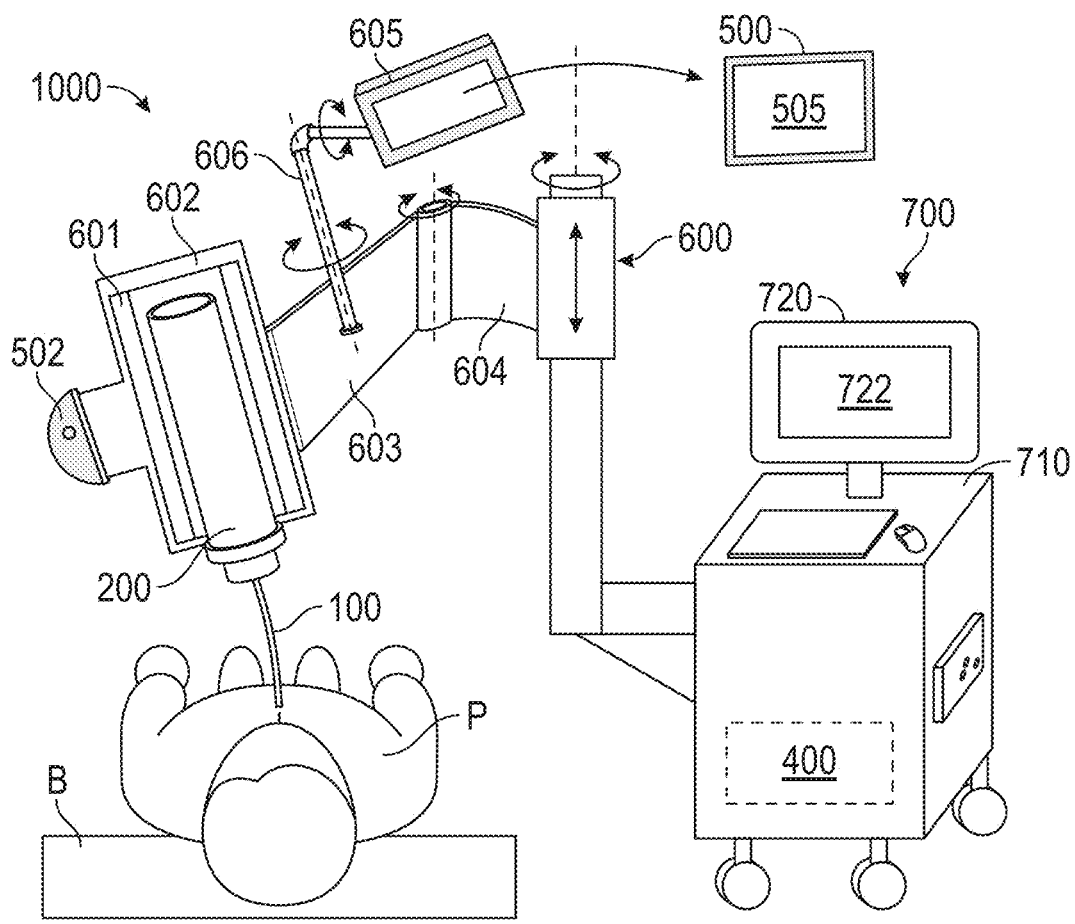
FIG. 7A shows an exemplary arrangement of a robotic endoscope system 1000 comprising a handheld portable display controller 500 attachable to a support platform 600, according to one embodiment.

FIG. 7A illustrates a robotic endoscope system 1000 with an embodiment of the support platform 600 for controlling an endoscope probe 100 using the handheld portable display controller 500 in manual mode or robot mode. In this embodiment, the display section 505 of the portable display controller 500 (handheld monitor) is removably mounted in a monitor receptacle 605 which is attached to a repositionable support arm 606. The control section 502 is separated from the display section 505, and mounted on a side of the support plate 602. This arrangement can be advantageous in order for the user to optimize viewing angles and ease of movement during the operation of the system.

Specifically, according to FIG. 7A, the robotic endoscope system 1000 includes a console 700 comprised of a computer cart 710 and a main display device 720. The computer cart 710 encloses therein the computer system 400. The main display device 720 may include a screen 722 (corresponding to screen 422 described in FIG. 1A). The support platform 600 is a multi-link robotic arm attached to the computer cart 710 of console 700. The support platform 600 includes the support plate 602, a linear stage 601, a first arm link 603, a second arm link 604, a repositionable articulated arm 606, and a monitor receptacle 605. The monitor receptacle 605 can be provided with magnetic contacts or spring loaded snap-on brackets configured to hold therein the portable display controller 500 in a secure, but removable manner. The articulate arm 606 can have a plurality of secondary links with various degrees of freedom in order for the user to optimize viewing angles of the display section 505 (screen) during the operation of the system.

The robotic endoscope system 1000 is configured to perform an endoscopy procedure on a patient (P) which is disposed on a medical table or bed (B). To that end, similar to other embodiments, the user (not shown in FIG. 7A) may use a control section 502 (e.g., a handheld joystick controller) to perform initial manual insertion of the endoscope probe 100 to a predetermined location of the patient's anatomy (e.g., the user may perform manual insertion of a bronchoscope to the first carina of a patient), while observing the manual insertion on the display section 505 (a display screen) of the portable display controller 500. In addition, the portable display controller 500 and the control section 502 can be configured to be combined with each other and with the handle 200, e.g., to form a single controller (as shown in FIG. 3A), so that the user can use both the control section 502 and screen display section 505 for manual insertion as previously described. After the manual portion of the procedure is completed (after the manual mode), the user can return the control section 502, the handle 200, and the display section 505 of portable controller 500 to their respective positions on the support platform 600. As soon as the endoscope handle 200 is returned to the support plate 602, the control system 300 takes over the robotic control (enters robot mode) to robotically navigate the probe for the remainder of the procedure. In robot mode, the controller 320 kinematically controls the actuators or motors to bend, twist or rotate the probe via one or more of the control wires 110.

In robot mode, the robotic control system 300 (or a separate control system) may also control the movement of one or more robotic arms or links of the support platform 600. The robotic control system 300 may receive sensor data from each robotic arm or link thereof indicating current parameters of the robotic arm or link thereof (e.g., position, joint angles, measured forces, etc.) and may send control signals to actuators (gears, belts, magnets) to drive the movement of the arm 610 or links 603, 604, and 606. A motion tracking system (not shown) may track the position and orientation of the robotic arm and links thereof to determine the position of the support plate 602 within the coordinate system of the patient. A control loop, which may be executed using the image-guided procedure of the endoscope probe 100, the motion tracking system (not shown), and the robotic control system 300, may continuously read position and orientation data of the endoscope probe 100 and the robot arm parameters data and may send controlling signals to the robotic control system 300 to cause the robot support platform 600 to move the support plate 602, the linear stage 601, robot arm 610, and/or the monitor receptacle 605 to a desired position and orientation to optimize viewing angles and navigation control.

In this embodiment, display device 720 may be a primary display device (e.g., a main monitor) that may be connected to the endoscope handle 200 by a wired or wireless link (e.g., cable bundle 220 shown in FIG. 3A-3C). In one embodiment, the system console 700 may receive live-view image data (video data) from the endoscope probe 100, e.g., via the cable bundle 220, and output the video data to the main display device 720 and to the portable display controller 500 over a suitable video data interface (e.g., an HDMI interface) and may also exchange other signals with the display device over a separate data connection (e.g., a USB connection). In addition or alternatively, the portable display controller 500 may the receive live-view image data (video data) from the endoscope probe 100, e.g., via wired or wireless data communication.

Figure 7B:
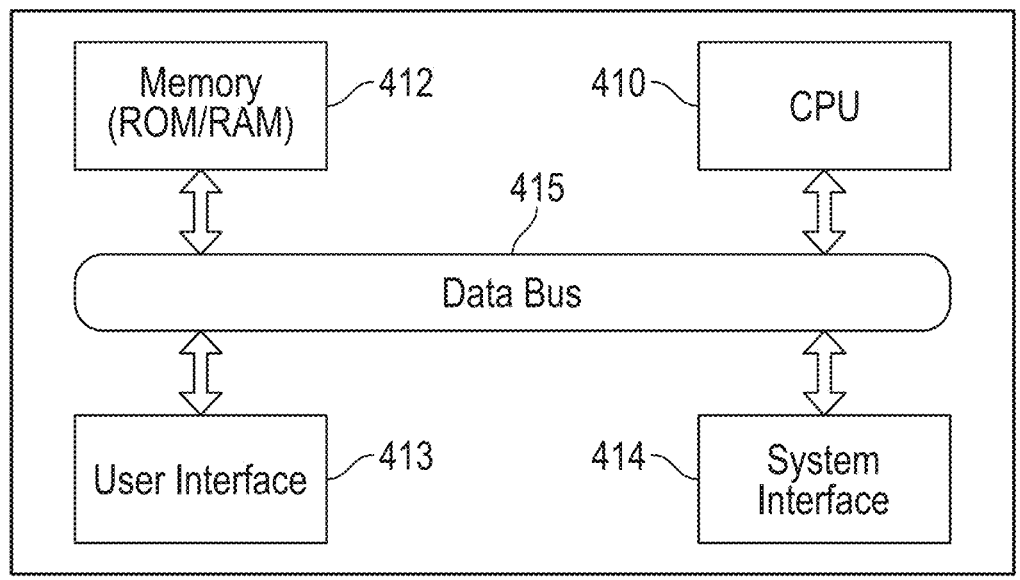
FIG. 7B illustrates functional blocks of computer system 400 (shown in FIG. 1A) which may also operate or be part of the portable display controller 500.

FIG. 7B illustrates functional blocks of computer system 400 (shown in FIG. 1A) which may also operate or be part of the portable display controller 500. As shown in FIG. 7B, the computer system 400 may include, among other things, a central processing unit (CPU) 410, a storage memory 412 including volatile random access memory (RAM) and non-volatile read only memory (ROM), a user input/output (I/O) interface 413, and a system interface 414 which are operatively interconnected via a data bus 415. The computer system 400 can be programmed to issue control commands which can be transmitted to the various parts of the control system 300, the system controller 320, the endoscope handle 200, and/or the display controller 500, e.g., upon receiving a user input via the user interface 413. A touch panel screen, a key board, mouse, joystick, ball controller, and/or foot pedal can be included as part of the user interface 413. For example, the display device 420 and GUI 422 shown in FIG. 1A can be part of the user interface 413. Using the user interface 413, the user can issue a command to cause the control system 300 to actively operate the steerable probe 100. For example, when a user inputs a command via the user interface 413, the command is transmitted to the central processing unit CPU 410 for execution of a given program routine thereby causing the CPU 410 to send a command via the system interface 414 to one or more of the motors or actuators in the actuator system 310, the linear stage 601, or to read signals output form one or more strain sensor 304 and/or EM sensor 190.

The CPU 410 may include one or more microprocessors (processors) configured to read and perform computer-executable instructions stored in the storage memory 412. The computer-executable instructions may include program code for the performance of the novel processes, methods and/or calculations disclosed herein. In particular, computer-executable instructions may include program code for executing the processes illustrated in FIG. 8A, FIG. 8B, and FIG. 9 to implement the real-time and seamless transition of manual mode and robot mode control of the endoscope probe 100.

The storage memory 412 includes one or more computer readable and/or writable media, which may include, for example, a magnetic disc (e.g., a hard disk), an optical disc (e.g., a DVD, a Blu-ray), a magneto-optical disk, semiconductor memory (e.g., a non-volatile memory card, flash memory, a solid state drive, SRAM, DRAM), an EPROM, an EEPROM, etc. Storage memory 412 may store computer-readable data and/or computer-executable instructions.

The system interface 414 provides electronic communication interface to input and output devices. In particular, system interface 414 may include one or more electronic circuits, such as a field-programmable gate array (FPGA) circuit boards to interface the computer system 400 with the motors or actuators that operate the control wires 110. The system interface 414 may also include interface connections for communication cables and a network port (either wired or wireless).

As it will be appreciated by a person of ordinary skill in the art, the location of the processor for the portable display control device is not necessarily limited to the described structures. A processor or computer, as illustrated in FIG. 7B, could be located in the controller 500 itself, on the handle 200, in the cart (as shown in FIG. 7A), or maybe even located on a network such as when using cloud-based processing. Moreover, the portable display controller 500 can be configured to take advantage of augmented computing capabilities by proprietary artificial intelligence (AI) tools that can help identify regions of interest for actuation and navigation of the probe 100 based on endoscope imaging cases performed in referential subject all around the world. Furthermore, portable display controller 500 and/or robotic system can two or more processors and operating systems: one for the back-end and another for the front end, e.g., for the touch screen user interface. The processor for this user input device could be built into the device itself (like a Nintendo Switch) or the user input device could be simply a touch screen whose processor is somewhere else.

Figure 8A:
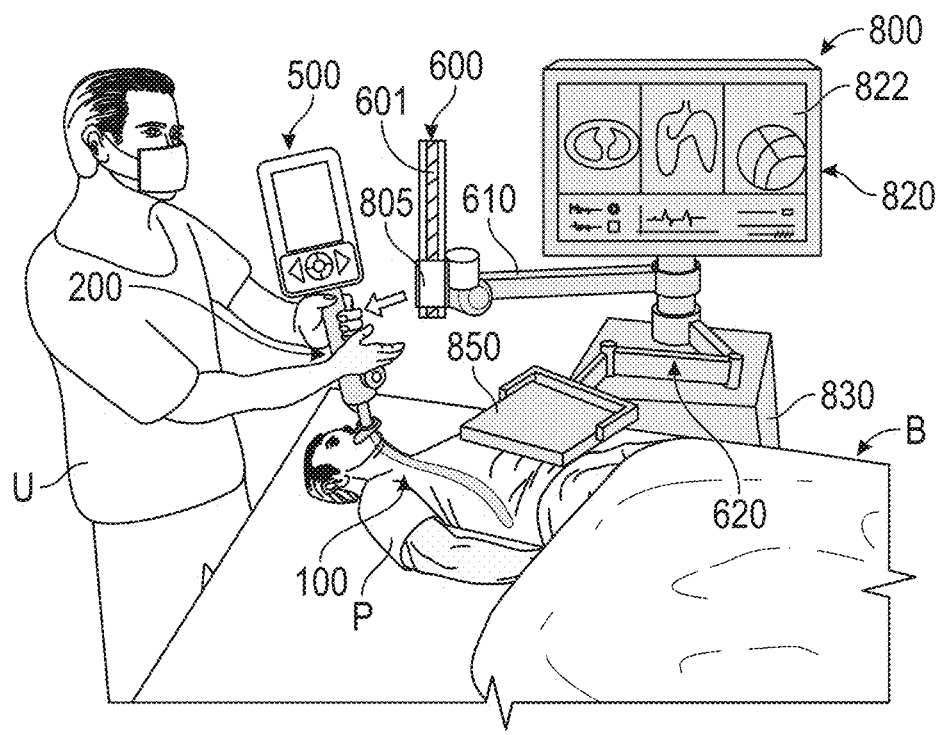
FIG. 8A shows an exemplary arrangement of a robotic endoscope system 1000 comprising a handheld portable display controller 500 attachable to a support platform 600, operating in a manual mode.
Figure 8B:
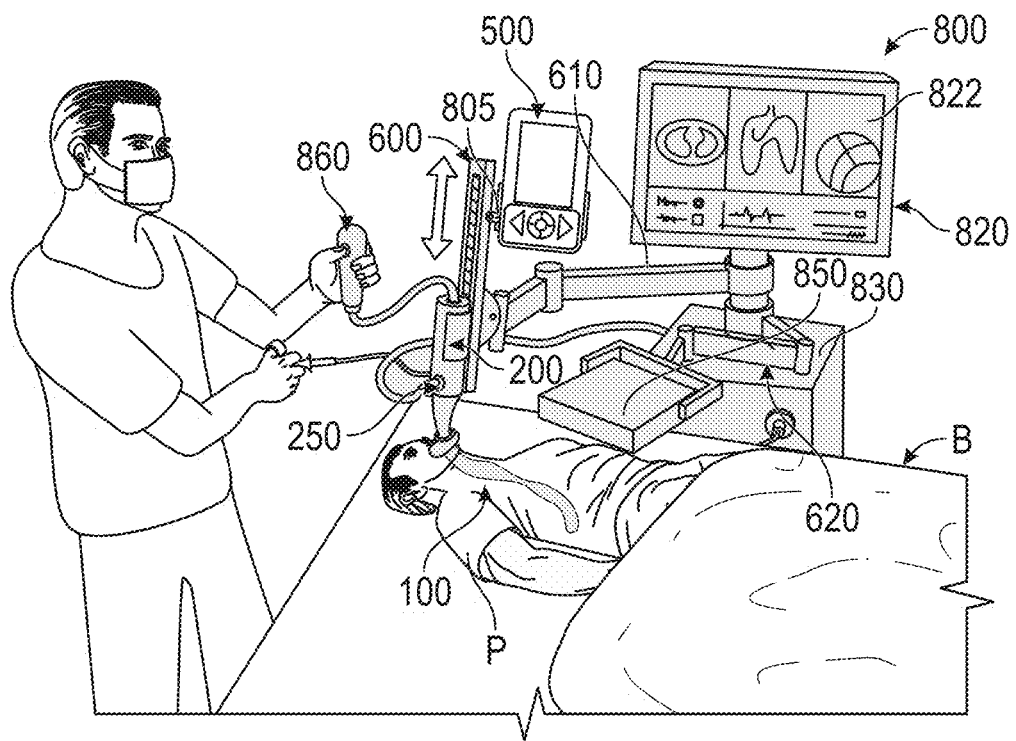
FIG. 8B shows the robotic endoscope system 1000 operating in a robot mode, according to one embodiment.

FIG. 8A and FIG. 8B illustrate a robotic endoscope system 1000 with a support platform 600 for controlling an endoscope probe 100 using the handheld portable display controller 500 in manual mode and robot mode, respectively, according to another embodiment. Design and usability of modern robotic endoscope systems strive to satisfy the user's needs, expectations, and limitations, at the same time as providing patient safety and fulfilling potential for market acceptance with a cost-effective solution. For example, it is not uncommon that a typical endoscopy procedure room would likely contain video monitor equipment, workstations, fluoroscopy equipment, automated medication dispensing stations, a patient bed, an anesthesia cart, and various storage cabinets, all interconnected by wiring and tubing connections. Therefore, new endoscope systems must accommodate to typical procedure workflows, constrained space limitations, and common procedural practices. In this regard, for example, it is important to satisfy recommend standards of button-size, foot-pedal location, and other human-robot interface parameters, such as weight, size, force requirements of a control interface to address the human factor needs of users and patients.

FIG. 8A and FIG. 8B illustrates a cart-mounted support platform embodiment, as an example of a proposed robotic endoscope system 1000 configured to satisfy most of a user's needs and patient's safety requirements. A cart-mounted support platform can advantageously provide compatibility with existing workflows. In addition, a small-sized handheld portable display controller (a mini-monitor) can provide additional functionality without taking up space in the crowded environment of a procedure room. According to FIG. 8A and FIG. 8B, a snake robot system configuration includes at least a cart-mounted support arm; and a bronchoscope-like or a gamepad type controller interface to operate a steerable endoscope probe 100 under an unattached manual insertion mode, and a robotic support platform attached robot mode.

Similar to previous embodiments, the robotic endoscope system 1000 includes a console 800, a cart-mounted support platform 600, a handle 200 attached to a proximal end of an endoscope probe 100, and a handheld portable display controller 500. A patient (P) disposed on a bed (B), in a supine position, is the subject of an endoscopic interventional procedure. The support platform 600 includes a first robot arm 610 and a second robot arm 620. The console 800 includes a modality cart 830 and a display device 820. The modality cart 830 includes the snake robot control unit (robot control system 300 shown in FIG. 1A). The display device 820 has a main display screen 822 (corresponding to display screen 422 of FIG. 1A) configured to provide a user with a graphical user interface (GUI) for interacting with and controlling the endoscope probe 100. The portable display controller 500 is normally docked on a monitor receptacle or clamp 805. The first robot arm 610 includes one or more actuated arm links configured to hold and position the linear stage 601 aligned with respect to the patient P. The second robot arm 620 includes one or more actuated arm links configured to hold and position an electromagnetic field generator 850. The EM field generator 850 is used in conjunction with the EM sensor 190 included in the catheter sheath to generate an EM tracking signal used for registration and/or navigation.

Under the manual mode, as shown in FIG. 8A, a user (U), for example, an endoscopist removes the endoscope handle 200 from the support platform 600, and attaches the portable display controller 500 to the proximal end of endoscope handle 200. The user then uses the combined portable display controller 500 connected to the handle 200 and endoscope probe 100 to perform a manual intubation (manual insertion) procedure in which the probe 100 is manually inserted to a predetermined location through an anatomy of a patient (P). The user can use the control section 502 of the portable display controller 500 to control the tip of endoscope probe 100 during the manual insertion mode. After manual insertion, the user returns the endoscope handle 200 to the support platform 600, and may also attach the portable display controller 500 to the display receptacle 805 on the robot arm 610. Under the manual mode, the user grips the handle 200 and/or the portable display controller 500 to dictate probe insertion/retraction. While the user is inserting the probe, the user is monitoring the camera view on the monitor (display section 505), while steering the probe tip using the catheter tip control. Once a predetermined anatomy is reached (e.g., once the first carina of the lungs is reached), the monitor/controller is detached, and the handle is returned to the support platform to initiate robot mode.

Under robot mode, as shown in FIG. 8B, the user now uses the monitor of the portable display controller 500 to observe the endoscope image, and the joystick to control the probe 100 for the remainder of the procedure. More specifically, under robot control mode, the system 300 controls the linear stage 601 to move the handle 200 in a linear direction L, while the user can still observe the images in the main display 822 or the display section 505 of the controller 500. In addition, during the robot mode, since the portable display controller 500 is attached to the robot arm 610, the user can continue to actuate the tip of the endoscope probe 100 with a separate joystick controller 860 while performing an interventional procedure (such as ablation) with a tool inserted through access port 250, as outlined in the process of FIG. 9 below.

<Control Method for Handheld Portable Display Controller>

Figure 9:
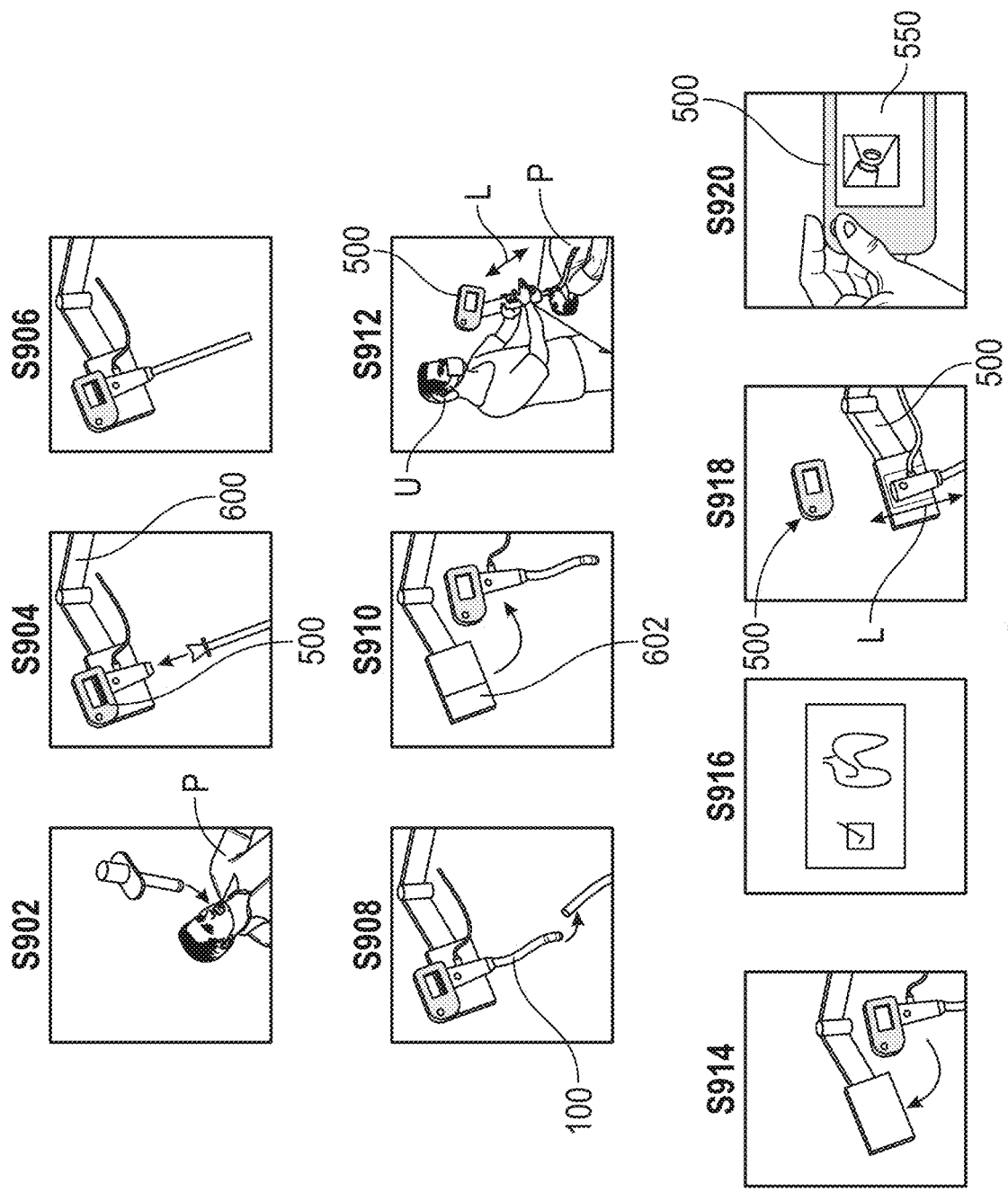
FIG. 9 shows an exemplary workflow which defines a process or method for manual insertion (manual mode) and robotically controlled navigation (robot mode) using a handheld portable display controller 500 in combination with the endoscope handle 200.

FIG. 9 shows an exemplary workflow which defines a process (method) for manual insertion and robotically controlled navigation using the handheld portable display controller 500, according to the various embodiments described above. When in manual mode, the user manually inserts and retracts the steerable endoscope probe 100, while the user controls the tip articulation by using actuators in the system with commands via a controller interface, such as a joystick or keypad. When in robot mode, besides the tip articulation, the user also uses the actuators to insert and retract the probe with commands via the controller interface. In both the manual mode and robot mode, the user has direct access to the display section 505 to observe, and optionally interact, with the endoscope images acquired by the probe.

According to the workflow of FIG. 9, at step S902, a patient preparation step occurs. For example, the user (an endoscopist) manually inserts an endotracheal tube into a patient (P). At step S904, the user attaches a new (sterile) catheter or probe 100 to the handle 200 which is already attached to the support platform 600. The new catheter or probe 100 is generally provided in a straight packaging sleeve. In addition, at step S904, the handheld portable display controller 500 is now connected to the endoscope handle 200. Next, at step S906, an auto-calibration process occurs. At step S906, because the catheter or probe 100 is provided in a straight packaging sleeve, the system can calibrate the positions of the control wires to a mean straight catheter position; this is an operation analogous to a "tare" process of a weighing scale, so that probe navigation can start from a known reference position and orientation. In this step, for example, in order to register the reference position and orientation of the probe, the system can control the imaging device 180 (camera) to initiate acquiring live-view images. Alternatively, the system can activate the EM tracking system to register the position and/or orientation of the EM sensor 190 with reference to the patient and/or bed coordinates.

At step S908, the user removes the straight packaging sleeve from the sterile catheter or probe 100. In other embodiments, the sterility of the catheter may be maintained via other processes or steps, so the packaging sleeve may not be used. At step S910, the user removes the combined handle 200 and portable display controller 500 from the support plate 602, and moves the assembled probe 100 and display controller 500 to the patient. At step S912, the user manually inserts the catheter or probe 100 to a predetermined location using manual steering controls (e.g. using the control section 502), while observing the procedure on the screen display section 505. For example, for a bronchoscopy procedure, the user manually inserts the catheter or probe 100 through the mouth of the patient (P) to the first carina, moving his arm in a linear direction L, while steering the tip of the probe with a joystick, control knob, or directional keypad of the control section 502. In this step, the user can observe the endoscope live-view image in the display section of the portable display controller 500. The processes of steps S910-S912 can be considered as a first procedure of the catheter or probe 100 in which the connected portable display controller 500 and handle 200 allow the user to use the control section 502 to manually steer the distal section of the probe while observing an image of the procedure in the display section 505 of the portable display controller 500. While this manual operation can be an almost linear insertion operation, there is still a need to steer the tip of the probe during the manual insertion to avoid or at least minimize patient discomfort. Here, the manual steering of the tip of the probe can be done via the joystick or keypad of control section 502.

After manually positioning the distal end of the probe at the predetermined location (first location), at step S914, the user brings the support platform 600 (e.g., by moving an articulated arm) closer to the patient's location and attaches the handle 200 and controller 500 back onto the support plate 602. Attaching the handle 200 onto the support platform 600 causes the system to enter robotic control mode. In some embodiments, attaching the handle 200 onto the support platform 600 may disable manual control mode. However, at step S916, the user can still use the portable display controller 500 and/or the main display device (820 in FIG. 8) of the console to confirm that the distal tip of the endoscope probe 100 has remained positioned at the desired initial location. Depending on the application, the process to confirm probe location can be done with an additional modality, for example, by endobronchial ultrasound (EBUS), or radial EBUS (REBUS), or by using EM data obtained from the EM generator 850 and EM sensor 190.

In other words, step S916 is a process to confirm (or register) the location of the probe's tip in the subject's anatomy (first carina location) with the software application of the robotic control system. After confirming the location of the probe's tip, the user can now detach the handheld portable display controller 500 from the handle 200 to continue probe navigation under robot controlled mode (step S918). In robot controlled mode, the robot control system 300 (robotic controller 320) controls the linear stage 601 in the support platform 600 (robotic arm) to linearly move the handle 200 in a direction L to continue moving the probe along the lumen of the patient's anatomy, while continuing to steer the tip of the probe 100.

At step S920, during robot controlled mode, the user can still use the joystick, keypad or knob controller of the control section 502 to navigate the tip of the probe 100 to the desired target lesion while continuing to acquire and observe the on-screen endoscopic images 500 on the display screen section 505 of the portable display controller 500. Alternatively, the screen section 505 of the portable display controller 500 may be used as a display to navigate to the target lesion using one or more of ultra-sound navigation, EM navigation, fluoroscopy, or the like. The process of steps S914-S920 can be considered as a second procedure of the probe 100 in which the portable display controller 500 remains in data communication with the handle 200 to allow the user to robotically control navigation (e.g., to remotely actuate the tip of the probe) inside the anatomy of the patient (e.g., using the control section 502 or using a touch screen GUI) while the robot control system 300 controls linear movement (insertion or retraction) of the probe.

In this manner, in the manual mode, the user manually inserts the probe tip towards a first location while controlling the tip of probe 100 using the handheld portable display controller 500, and in the robot mode, the robot control system controls the linear movement of the probe for robotic navigation from the first location to a second (target) location while the user can still control the orientation of the probe tip (if necessary). As noted above, controlling the probe tip can be effected by actuating control wires of the endoscope probe by a joystick controller or by a touch screen GUI in the display section of the portable display controller. In particular, a touchscreen display operative to control angulation of the tip probe and to display operations of the probe without the need for using traditional keyboard controls can lead to more efficient procedures without leaving the patient's bedside or shifting attention from the patient to communicate with assistant personnel or observe remotely mounted displays. Therefore, the ability to use a combined handheld portable display and manual controller device that can be efficiently attached and detached from the endoscope handle is considered of significant advantage over conventional technology.

The foregoing disclosure describes various embodiments of a handheld portable display controller 500 configured to interact with a robot support platform of a robotic endoscope system for combined manual insertion and robotic controlled navigation of an endoscope probe 100. The endoscope probe has a handle for the user to grip while manually inserting the catheter to a predetermined location (e.g., the first carina of the lungs). The handheld portable display controller 500 can be connected to the handle 200 for manual control. After manual insertions, the handle is attached to the support platform. This initiates robotic mode, where the insertion/retraction is controlled and moved by the support platform of the robotic system. When the system is in robotic mode, the handheld portable display controller can be detached from the handle and may be used to control the system and observe endoscope images of a procedure.

According to one embodiment, the handheld portable display controller 500 is a removable, tiltable monitor (a mini-monitor) with a joystick control for maneuvering the catheter tip during manual insertion. For manual insertion, the user grips the handle of the endoscope to control catheter insertion/retraction. While the user is inserting/retracting the catheter, the user is monitoring the camera view on the monitor, while steering the tip using the joystick. In an exemplary procedure, once the first carina of the lungs is reached, the monitor/controller is disconnected from the handle, and the handle is attached to the support platform to initiate robot control mode. Under robot mode, the user can use the portable display controller to control the navigation of the probe and observe live-view images for the remainder of the procedure.

Under manual mode, robotic system control is not available, but the portable display controller provides simple actuation controls such as up/down and left/right actuation of the probe to the user. Advantageously, the manual mode requires Low Cognitive load, as it provides basic functions without causing confusion for the physician. In addition, manual mode provides avoidance of use error—because it is so simple, it avoids use related errors that come from complicated user interfaces. Speed—It's fast and relatively easy for endopscopists to navigate to the first carina today with non-motorized endoscopes and their near-instantaneous responsiveness. SNAKE robot systems are motorized and rigidly mounted to complex robotic arm platforms, so it is much much slower than an endoscope operated by hand. By keeping the feature list small and similar to what endoscopists are used to, the controller makes insertion much faster than it would be if the user had to navigate to the first carina using robot mode. Ergonomics—The controller is a lightweight device in the physician's hand (not a giant endoscope that they have to hold perfectly still at a weird angle or lose their spot). Also, by having handheld monitor, the physician can focus on the patient and the procedure without looking across room.

Under robot mode, robotic control mode is fully enabled for linearly advancing or retracting the probe, and the portable display controller continues to provide simple controls such as up/down and left/right actuation, as well as advanced "follow-the-leader" or "chicken head" actuation of the probe to the user. In this manner, robot mode enables more advanced functionality. Specifically, the controller makes advanced robotic functions possible, allowing physicians to reach places in an intuitive and interactive manner which was not previously possible. For example, in a case where the user decides "I want to go there", the user can touch the image on the screen where him/her wants the snake to go (e.g. pick a branch), and the probe tip goes there.

Software Related Disclosure

Embodiment(s) of the present disclosure can be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. An I/O interface can be used to provide communication interfaces to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

Other Embodiments or Modifications

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A method, comprising:
   connecting a portable display controller to an imaging probe;
   acquiring an endoscope image with the imaging probe and displaying the endoscope image on a display section of the portable display controller;
   manually inserting a distal end of the imaging probe through a lumen and advancing the imaging probe along a first part of the lumen until the endoscope image shows that the distal end of the imaging probe has reached a first location along a longitudinal path of the lumen;
   after reaching the first location, detaching the portable display controller from the imaging probe while continuing to acquire and display the endoscope image;
   attaching the imaging probe to a robotic support platform and establishing data communication between a robotic controller and a handle of the imaging probe; and robotically controlling the imaging probe with the robotic controller to advance the imaging probe along a second part of the lumen until the endoscope image shows that the distal end of the imaging probe has reached a second location different from the first location along the longitudinal path of the lumen.

2. The method according to claim 1,
wherein advancing the imaging probe along the first part of the lumen includes manually guiding at least one bending section of the imaging probe using a control section of the portable display controller, and displaying the endoscope image acquired by the imaging probe in the display section of the portable display controller.

3. The method according to claim 1,
wherein advancing the imaging probe along the first part of the lumen includes manually guiding the distal end of the imaging probe using a joystick controller provided in a control section of the portable display controller, and displaying the endoscope image acquired by the imaging probe in the display section of the portable display controller.

4. The method according to claim 1,
wherein advancing the imaging probe along the second part of the lumen includes robotically moving the handle of the imaging probe using the robotic controller while steering the distal end of the imaging probe using a control section of the portable display controller.

5. The method according to claim 1,
wherein advancing the imaging probe along the second part of the lumen includes robotically moving the handle of the imaging probe in a linear direction using the robotic controller while bending the distal end of the imaging probe in a curved direction using a control section of the portable display controller or a joystick controller other than the portable display controller.

6. The method according to claim 1,
wherein connecting the portable display controller to the imaging probe includes establishing wired data communication between a connection terminal of the portable display controller and the handle of the imaging probe.

7. The method according to claim 1,
wherein connecting the portable display controller to the imaging probe includes establishing wireless data communication between a wireless transceiver of the portable display controller and a wireless transceiver of the handle of the imaging probe.

8. The method according to claim 1,
wherein connecting the portable display controller to the imaging probe includes physically attaching the portable display controller to the handle of the imaging probe and establishing data communication between a connection terminal of the portable display controller and the handle of the imaging probe.

9. The method according to claim 8, further comprising:
detaching the portable display controller from the handle of the imaging probe without interrupting data communication between the portable display controller and the handle of the imaging probe;
attaching the portable display controller to the robotic support platform; and
displaying the endoscope image acquired by the imaging probe in the display section of the portable display controller.

* * * * *